US012589166B2

(12) United States Patent     (10) Patent No.:   US 12,589,166 B2

Hernandez et al.     (45) Date of Patent:    Mar. 31, 2026

(54) COMPOSITIONS AND METHODS FOR TREATING WOUNDS

(71) Applicant: Rutgers, The State University of New Jersey, New Brunswick, NJ (US)

(72) Inventors: Maricely Ramirez Hernandez, Linden, NJ (US); Tewodros Asefa, Kendall Park, NJ (US); Jeffrey Boyd, New Brunswick, NJ (US); Javiera Norambuena-Morales, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 528 days.

(21) Appl. No.: 17/925,458

(22) PCT Filed: May 13, 2021

(86) PCT No.: PCT/US2021/032211

§ 371 (c)(1),
(2) Date: Nov. 15, 2022

(87) PCT Pub. No.: WO2021/231702

PCT Pub. Date: Nov. 18, 2021

(65) Prior Publication Data

US 2023/0181760 A1     Jun. 15, 2023

Related U.S. Application Data

(60) Provisional application No. 63/025,306, filed on May 15, 2020.

(51) Int. Cl.
A61K 47/69     (2017.01)
A61K 9/00     (2006.01)
(Continued)

(52) U.S. Cl.
CPC ........ A61K 47/6923 (2017.08); A61K 9/0014 (2013.01); A61K 33/34 (2013.01);
(Continued)

(58) Field of Classification Search
CPC .......................... A61K 47/6923; A61K 9/0014
See application file for complete search history.

(56) References Cited

U.S. PATENT DOCUMENTS 8,715,745 B2   5/2014   Young et al.
9,040,586 B2   5/2015   Da Rocha
(Continued)

FOREIGN PATENT DOCUMENTS

CN     103940792 B    6/2016
FR     2461495 A1    2/1981
(Continued)

OTHER PUBLICATIONS

Zhou et al (Tuning the Growth, Crosslinking, and Gelling of Disulfide Containing PGMAs On the Surfaces of Mesoporous Silica Nanoparticles for Redox/pH Dual Controlled Cargo Release, Polymer Chemistry, vol. 7, pp. 2171-2179. (Year: 2016).*
(Continued)

*Primary Examiner* — Carlos A Azpuru
(74) *Attorney, Agent, or Firm* — Saul Ewing, LLP; Domingos J. Silva; Kevin O'Brien

(57) ABSTRACT

The present disclosure relates to compositions and methods of treating a wound, or location of interest, in a subject by topically administering to the subject the therapeutic composition of the disclosure. The composition of the disclosure comprises nanoparticle (NP) composites for delivering one or more therapeutic agents to the wound.

19 Claims, 19 Drawing Sheets

Tailoring different pore sizes

Drug loading

Tailoring different pore sizes

Drug A
Drug B
Enlarged pore

Polyethyleneimine (PEI) grafting

= PEI

(51) Int. Cl.

| | |
|---|---|
| *A61K 33/34* | (2006.01) |
| *A61K 36/886* | (2006.01) |
| *A61K 47/32* | (2006.01) |
| *A61K 47/36* | (2006.01) |
| *A61K 47/42* | (2017.01) |
| *A61K 47/44* | (2017.01) |
| *A61P 17/02* | (2006.01) |
| *A61P 31/02* | (2006.01) |

(52) U.S. Cl.
CPC ............ *A61K 36/886* (2013.01); *A61K 47/32* (2013.01); *A61K 47/36* (2013.01); *A61K 47/42* (2013.01); *A61K 47/44* (2013.01); *A61P 17/02* (2018.01); *A61P 31/02* (2018.01)

(56) References Cited

U.S. PATENT DOCUMENTS

| | | |
|---|---|---|
| 2010/0081773 A1 | 4/2010 | Multhaup et al. |
| 2013/0171225 A1 | 7/2013 | Uhlmann et al. |
| 2014/0039068 A1 | 2/2014 | Bronich et al. |
| 2018/0147177 A1 | 5/2018 | Bastos et al. |
| 2018/0256709 A1 | 9/2018 | Zepp et al. |
| 2018/0344641 A1 | 12/2018 | Brinker et al. |
| 2020/0038525 A1 | 2/2020 | Jermy et al. |

FOREIGN PATENT DOCUMENTS

| | | |
|---|---|---|
| WO | 200164222 A1 | 9/2001 |
| WO | 2010068275 A1 | 6/2010 |
| WO | 2017120098 A1 | 7/2017 |

OTHER PUBLICATIONS

Ianova, et al., "Layer-by-Layer Decorated Nanoparticles with Tunable Antibacerial and Antibiofilm Properties against Both Gram-Positive and Gram-Negative Bacteria", ACS Appl Mater Interfaces, vol. 10, 2018, pp. 3314-3323.

Lee, et al., "Visualization of MMP-2 Activity Using Dual-Probe Nanoparticles to Detect Potential Metastatic Cancer Cells", Nanomaterials, 8(119), 2018, pp. 1-12.

Zhou, et al., "Tuning the growth, crosslinking, and gating effect of disulfide-containing PGMAs on the surfaces of mesoporous silica nanoparticles for redox/pH dual-controlled cargo release", Polym Chem, vol. 7, 2016, pp. 2171-2179.

PCT International Search Report & Written Opinion dated Sep. 22, 2021 for corresponding PCT International Application PCT/US2021/032211.

Croissant, J.G., et al., "Mesoporous Silica and Organosilica Nanoparticles: Physical Chemistry, Biosafety, Delivery Strategies, and Biomedical Applications", Advanced Healthcare Materials, vol. 7, No. 4, pp. 1-75, 2017.

Pawlaczyk, M., et al., "Nanomaterials Modification by Dendrimers—A Review", World Journal of Research and Review (WJRR), , vol. 6, Issue-5, pp. 14-30, May 2018.

Partial Supplementary European Search Report issued Sep. 16, 2024 in European Patent Application No. 21804571.4.

Extended European Search Report issued Dec. 9, 2024 in European Patent Application No. 21804571.4.

Domalaon, et al., "Synergistic combinations of anthelmintic salicylanilides oxyclozanide, rafoxanide, and closantel with colistin eradicates multidrug-resistant colistin-resistant Gram-negative bacilli", Journal of Antibiotics, 72(8), 2019, pp. 605-616.

Meng, et al., "Self-Association of Rafoxanide in Aqueous Media and Its Application in Preparing Amorphous Solid Dispersions", Mol Pharm, 14(5), 2017, pp. 1790-1799.

Zhitnitsky, et al., "The highly synergistic, broad spectrum, antibacterial activity of organic acids and transition metals", Scientific Reports, 7, 2017, pp. 44554.

* cited by examiner

Tailoring different pore sizes

Tailoring different pore
sizes

Drug loading

Drug A
Drug B
Enlarged pore

Polyethyleneimine (PEI) grafting

= PEI

COMPOSITIONS AND METHODS FOR TREATING WOUNDS

CROSS-REFERENCE TO RELATED APPLICATIONS

This application is a 35 U.S.C. § 371 national phase application from, and claims priority to, PCT International Patent Application No. PCT/US2021/032211, filed May 13, 2021, which claims priority under 35 U.S.C. § 119 (e) to U.S. Provisional Patent Application No. 63/025,306, filed May 15, 2020, all of which are hereby incorporated herein by reference in their entireties.

BACKGROUND

A wound may constitute variety of insults or damages to a body tissue. For example, a wound may involve a laceration, cut or scrape, surgical incision, sore, thermal burn, puncture, or decubitus ulcer, e.g., bed sores. The amount of money spent on wound care, the loss of productivity for afflicted individuals and the families that care for them, and their diminished quality of life come at great cost to society. An estimated excess of 25 billion U.S. dollars is spent annually on treatment of chronic wounds, and the burden is rapidly growing due to increasing health care costs, an aging population, and a sharp rise in the incidence of diabetes and obesity worldwide.

One of the main factors for development of chronic wounds is the presence of biofilm on the wound, with 60-100% of chronic wounds being affected by these biofilms. The biofilm is a protective matrix composed of polymers produced by various species of microorganisms. The biofilm adheres to surfaces of the wound, hampering administration of therapeutic agents to the site of the wound. Additionally, due to an increased antimicrobial resistance to conventional antibiotics, there is an increased interest in developing materials that can more effectively deliver antimicrobial agents to the wounds.

It thus follows that there exists a need in the art for novel compositions that provide economical and relatively efficacious wound healing for subjects in need thereof. The present disclosure fulfills this need.

BRIEF SUMMARY

In one aspect, the present disclosure relates to a nanoparticle (NP) functionalized with at least one pH-responsive polymer and/or copolymer, wherein at least one cargo is associated with the NP and/or the at least one pH-responsive polymer/copolymer, and wherein swelling of the at least one pH-responsive polymer and/or copolymer allows for release of the at least one cargo from the NP or the polymer and/or copolymer comprising the cargo. In certain embodiments, the NP comprises a silica nanoparticle (SNP) or a titania nanoparticle (TNP). In certain embodiments, the NP is a porous NP comprising a plurality of pores. In certain embodiments, the NP is a non-porous nanoparticle. In certain embodiments, the cargo comprises a therapeutic cargo. In certain embodiments, the therapeutic cargo is a metal NP. In certain embodiments, the metal NP comprises copper and/or silver. In certain embodiments, the copper is selected from the group consisting of Cu(I), Cu(II), and Cu⁰. In certain embodiments, the Cu(I), Cu(II), or Cu⁰ is derived from Cu(I) acetate (CuOAc), Cu(II) acetate (Cu(OAc)₂), or Cu(II) chloride (CuCl₂).

In another aspect, the present disclosure provides a composition comprising about 0.10% to about 0.25% of chitosan, about 0.10% to about 2.0% of sodium alginate, about 0.1% to about 0.5% of gelatin, about 0.01% to about 1% of grapeseed oil, polyvinyl alcohol (PVA), and aloe vera gel, wherein the composition is formulated for application to a wound for promoting healing of the wound. In certain embodiments, the composition further comprises the nanoparticle (NP) of the present disclosure.

In yet another aspect, the present disclosure provides a method of healing a wound of a subject, the method comprising administering to the wound an effective amount of the composition of the present disclosure. In certain embodiments, the wound is a burn wound.

BRIEF DESCRIPTION OF THE DRAWINGS

For the purpose of illustrating the disclosure, there are depicted in the drawings certain embodiments of the disclosure. However, the disclosure is not limited to the precise arrangements and instrumentalities of the embodiments depicted in the drawings.

FIG. 4A: Photo of Cu²⁺ ions-impregnated SBA-15 shows a powdered material with a blue cast, indicating the anchoring of the Cu²⁺ ions in the amine-groups of N-(2-aminoethyl)-3-aminopropyltrimethoxysilane (DAMO)-SBA-15. FIG. 4B: Photo of Cu/SBA-15 shows a reddish-brown color indicating the presence of Cu⁰ nanoparticles inside the SBA-15, which are formed from the reduction of Cu²⁺ ions by ascorbic acid.

DETAILED DESCRIPTION

Figure 1A:
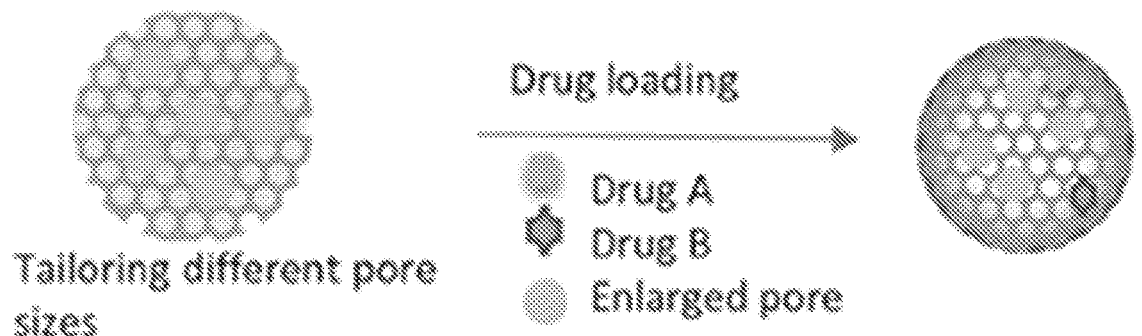
FIGS. 1A-1B provide illustrations of polymer functionalized nanoparticles of the disclosure.
Figure 1A:
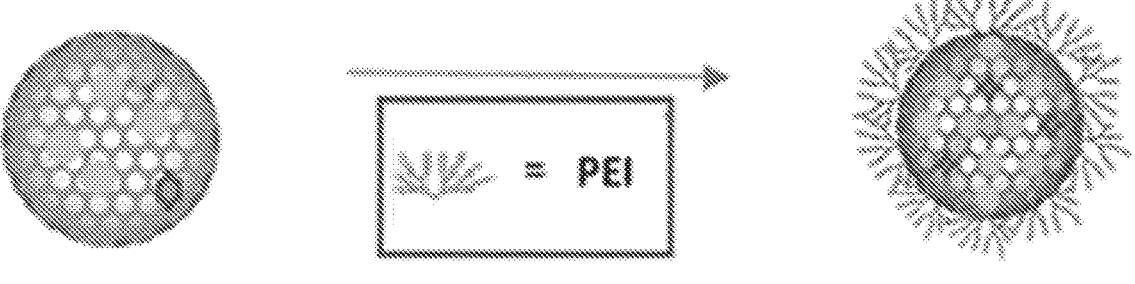
Figure 1B:
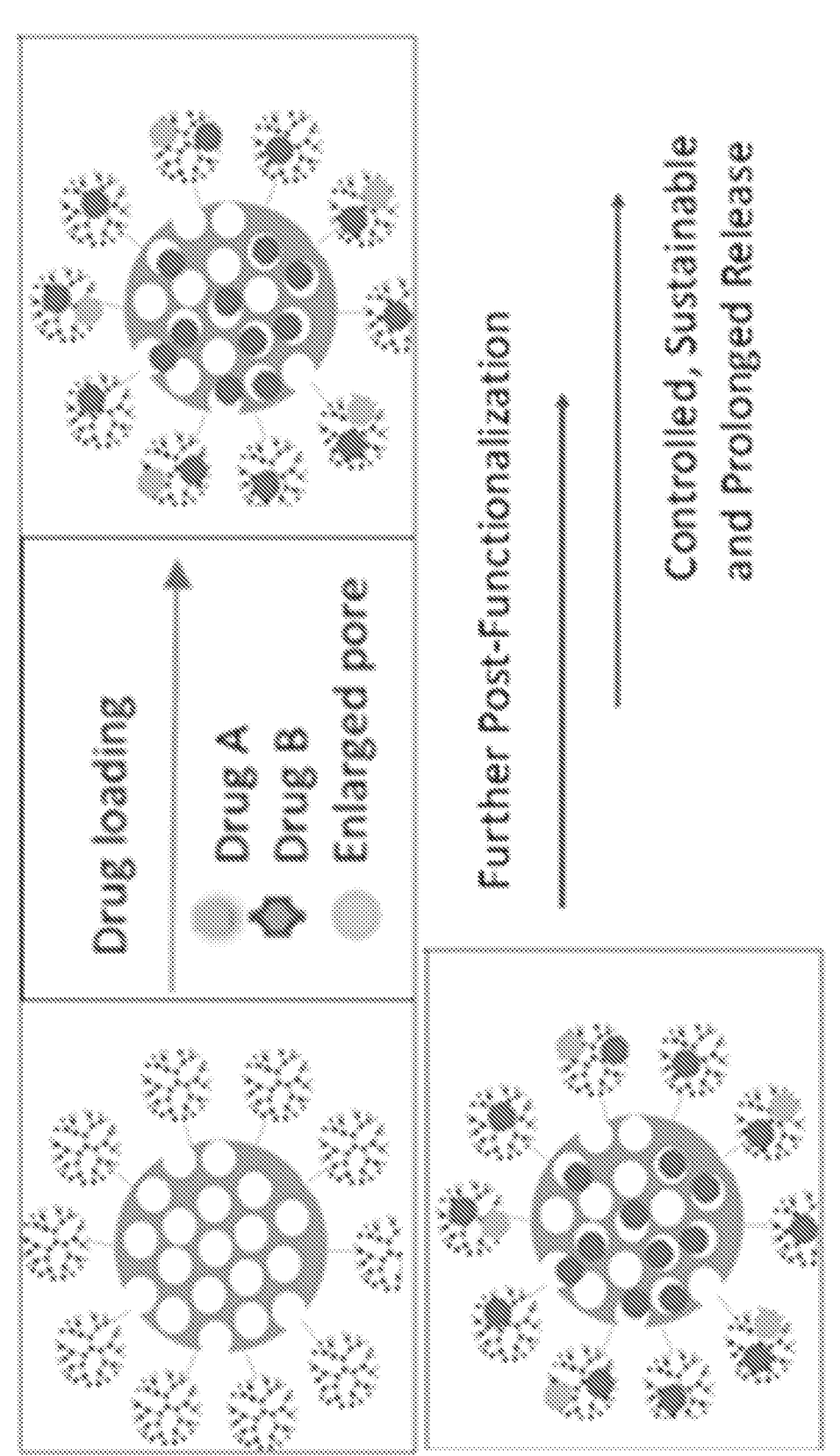
Figure 1C:
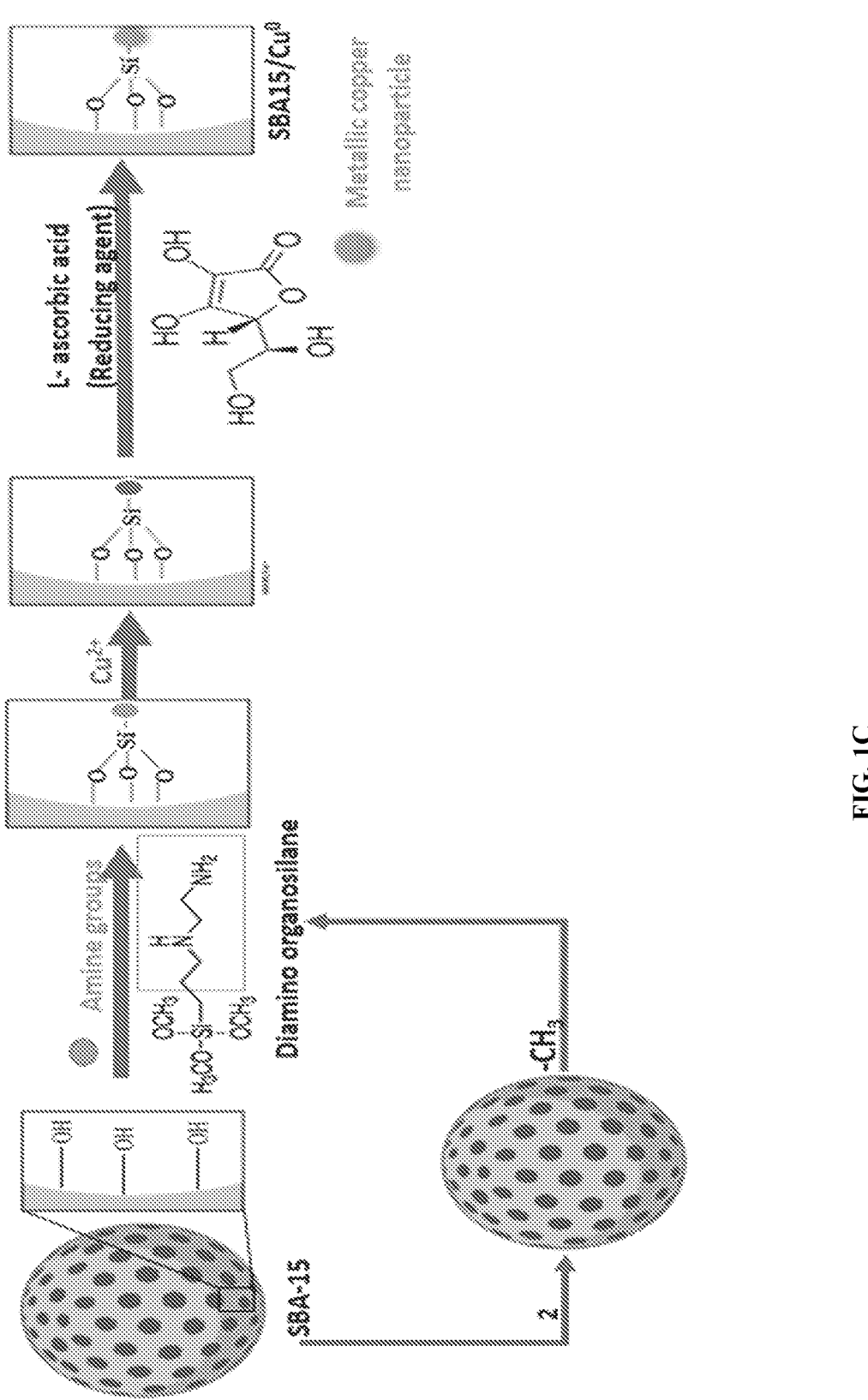
FIG. 1C: synthetic procedure used to produce different copper-loaded SBA-15 materials; Step 1: corresponds to the synthesis of non-methyl capped SBA-15; and Step 2: corresponds to the functionalization of SBA-15 with methyl (—CH₃) groups, wherein the subsequent steps correspond to diamino (DAMO) functionalization, followed by impregnation of copper ions, and finally reduction of copper ions to metallic copper using L-ascorbic acid as a reductant.
Figure 2:
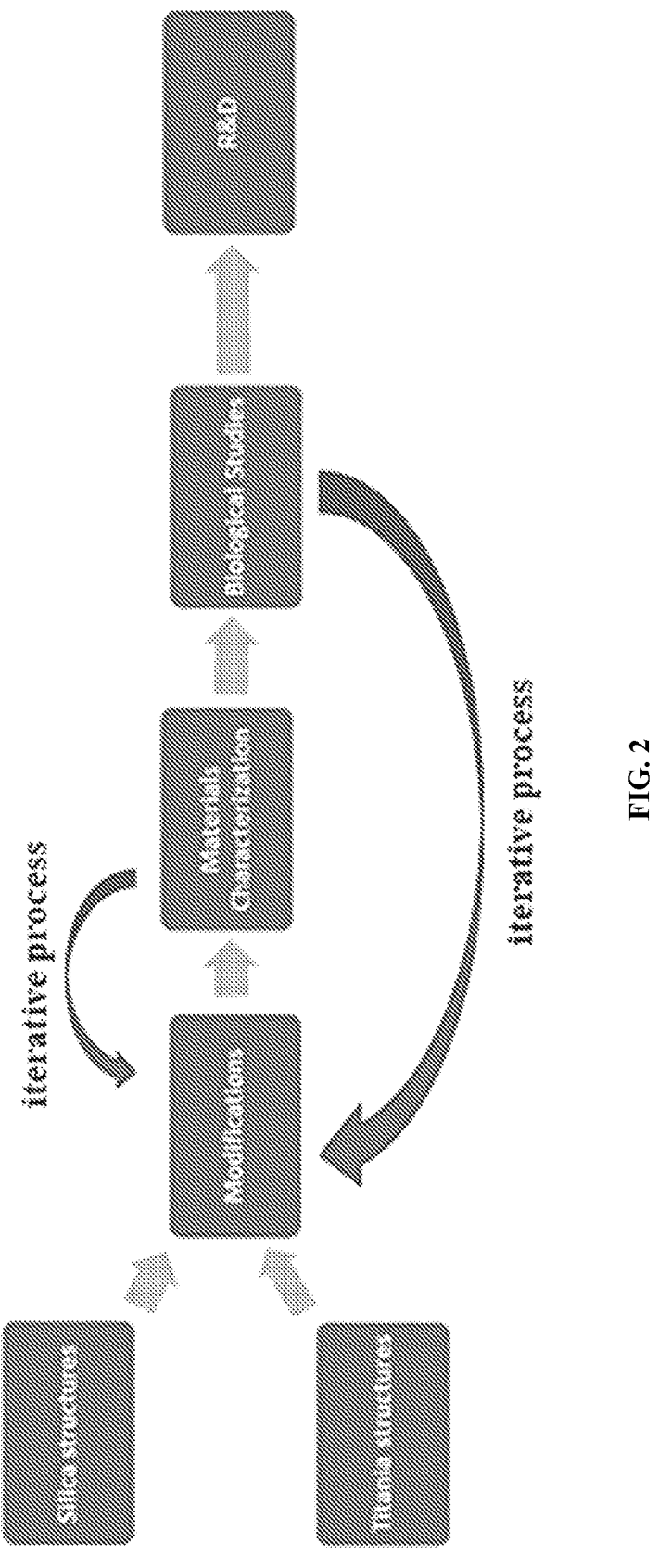
FIG. 2 is a schematic showing steps involved in developing nanoparticles of the disclosure. Non-limiting examples of silica structures include MCM-41, SBA-15, and colloidal silica. Non-limiting examples of parameters subject to modification include particle size, particle shape, pore size, as well as the chemical and physical surface. Non-limiting examples of parameters used for material characterization include size, morphology, drug loading and release, thermal stability, gaseous exchange, and H₂O permeability. Non-limiting examples of biological studies include cytotoxicity, biocompatibility, epithelial cell proliferation, antimicrobial activity, and microbial detection. Non-limiting examples of research and development (R&D) include drug delivery, drying time, flexibility, and adhesion.
Figure 3:
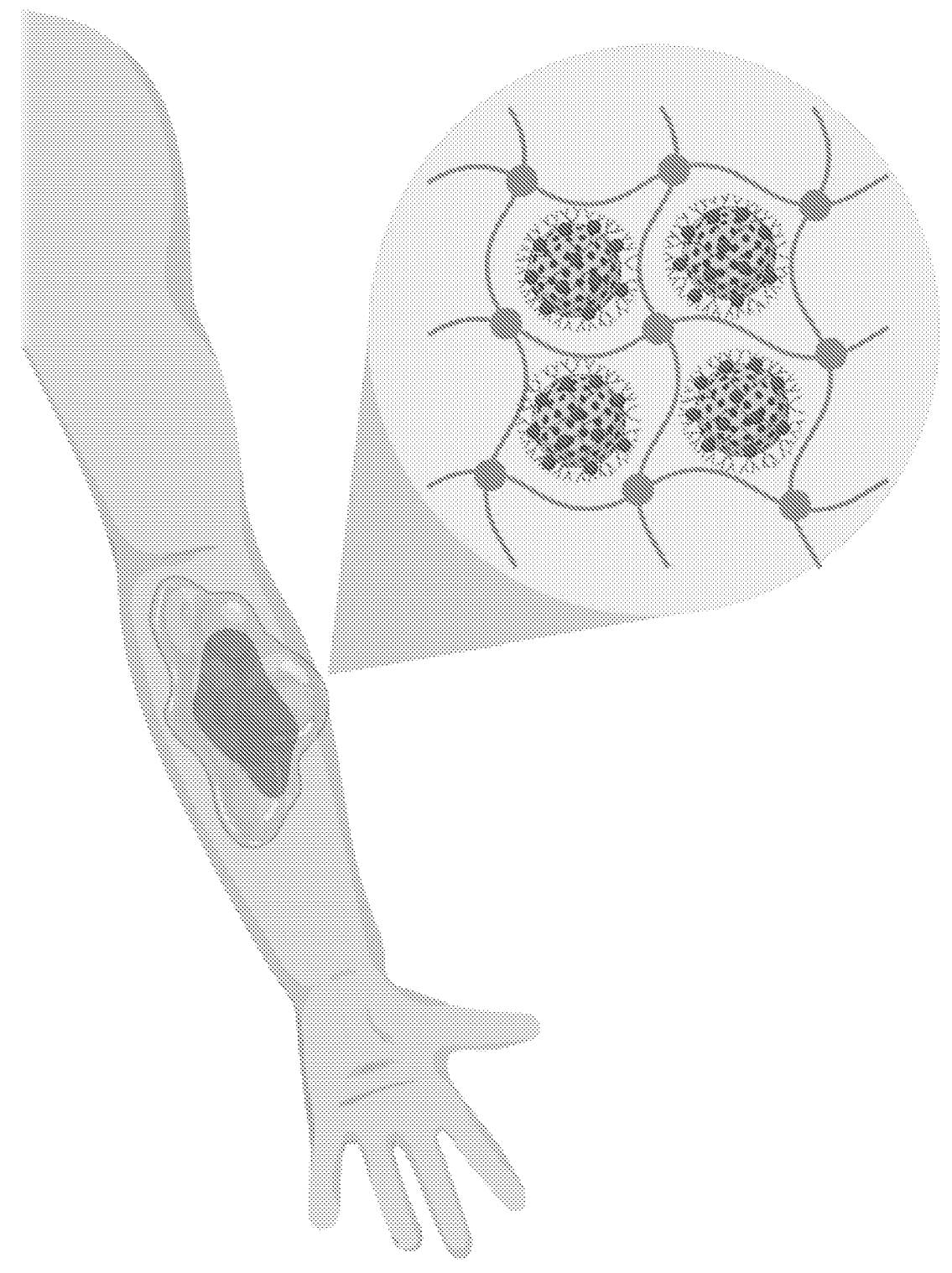
FIG. 3 provides an illustration of the functionalized nanoparticles of the disclosure dispersed in an excipient which is topically applied on a human skin wound.

The present disclosure relates to compositions and methods for dressing a wound and promoting healing of the wound in a subject.

Definitions

As used herein, each of the following terms has the meaning associated with it in this section.

Unless defined otherwise, all technical and scientific terms used herein generally have the same meaning as commonly understood by one of ordinary skill in the art to which this disclosure belongs. Generally, the nomenclature used herein and the laboratory procedures in organic chemistry, formulation chemistry, and biology are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biocompatible" as used herein refers to the ability of a material to perform appropriately when in contact with living tissue without damaging the material or the tissue which are in contact, or any further tissue and/or component of the organism in which the material is direct or indirect contact with.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "dendrimer" or "dendrimeric" as used herein refers to highly ordered, branched polymeric molecules.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "to dress a wound" refers to the act of applying an adjunct to the wound, in order to improve healing and/or prevent further harm.

As used herein, the term "effective" means adequate to accomplish a desired, expected, or intended result.

As used herein, the terms "effective amount," "pharmaceutically effective amount" and "therapeutically effective amount" refer to a nontoxic but sufficient amount of an agent to provide the desired biological result. That result can be reduction and/or alleviation of the frequency and/or severity of signs, symptoms, or causes of a disease, or any other desired alteration of a biological system. An appropriate therapeutic amount in any individual case may be determined by one of ordinary skill in the art using routine experimentation.

As used herein, the terms "inhibiting," "reducing," and variations of these terms, include any measurable decrease, such as but not limited to complete or substantially complete inhibition.

As used herein, the "instructional material" includes a publication, a recording, a diagram, or any other medium of expression that may be used to communicate the usefulness of the compounds of the disclosure. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the disclosure or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

As used herein, the term "or" means "and/or," unless explicitly indicated to refer to alternatives only or the alternatives are mutually exclusive, although the disclosure supports a definition that refers to only alternatives and "and/or."

As used herein, the terms "patient" and "subject" refer to a human or a non-human animals. Non-human mammals include, for example, livestock and pets, such as ovine, bovine, porcine, canine, feline and murine mammals. Preferably, the subject is human.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the disclosure with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

As used herein, the term "preventing" as relating to a condition in a subject refers to the ability of avoiding the onset of the condition in a patient that is likely, susceptible, or expected to develop the condition.

The term "therapeutic" as used herein means a treatment and/or prophylaxis. A therapeutic effect is obtained by suppression, remission, or eradication of a disease state.

As used herein, the term "topical" as applied to mode of administration includes but is not limited to "dermal." The term "dermal" refers to the application of a composition to the skin of a subject. The term "topical refers to the application of a composition to the body's natural surface, which has not been created by surgical intervention or any artificial means.

As used herein, the terms "treat," treating," "treatment," and the like, including "healing," refer to reducing or improving a disease or condition and/or symptom associated therewith. It will be appreciated that, although not precluded, treating a disease or condition does not require that the disease, condition or symptoms associated therewith be completely ameliorated or eliminated.

As used herein, the term "wound dressing" refers to an adjunct (such as a chemical and/or material) used by a person for application to a wound to promote healing and/or prevent further harm.

Throughout this disclosure, various aspects of this disclosure can be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5, and 6. This applies regardless of the breadth of the range.

The recitation of an embodiment for a variable or aspect herein includes that embodiment as any single embodiment or in combination with any other embodiments or portions thereof.

Compositions

In one aspect, the disclosure provides a novel, biocompatible nanoparticle (NP) for delivering cargoes to a wound. In another aspect, the disclosure provides a therapeutic composition comprising at least one NP of the disclosure for promoting healing of the wound. In yet another aspect, the disclosure provides a composition capable of promoting healing of wounds.

In certain embodiments, the NP is a silica NP (SNP). In certain embodiments, the NP is a titania NP (TNP). In certain embodiments, the SNP is MCM-41. In certain embodiments, the SNP is MCM-48 type mesoporous silica (having a size ranging from about 8 nm to about 1,000 nm). In certain embodiments, the MCM-48 type mesoporous silica has a size selected from the group consisting of about 8, 50, 100, 150, 200, 250, 300, 350, 400, 450, 500, 550, 600, 650, 700, 750, 800, 850, 900, 950, and about 1000 nm. In certain embodiments, the SNP is SBA-15 type mesoporous silica (having a size ranging from about 8 nm to about 1,000 nm). In certain embodiments, the SBA-15 type mesoporous silica has a size selected from the group consisting of about 8, 50, 100, 150, 200, 250, 300, 350, 400, 450, 500, 550, 600, 650, 700, 750, 800, 850, 900, 950, and about 1000 nm. In certain embodiments, the SNP is large pore mesoporous silica. In certain embodiments, the SNP is colloidal silica (having a size ranging from about 8 nm to about 1,000 nm). In certain embodiments, the colloidal silica has a size selected from the group consisting of about 8, 50, 100, 150, 200, 250, 300, 350, 400, 450, 500, 550, 600, 650, 700, 750, 800, 850, 900, 950, and about 1000 nm. In certain embodiments, the SNP is surface etched colloidal silica (having a size ranging from about 8 nm to about 1,000 nm). In certain embodiments, the surface etched colloidal silica has a size selected from the group consisting of about 8, 50, 100, 150, 200, 250, 300, 350, 400, 450, 500, 550, 600, 650, 700, 750, 800, 850, 900, 950, and about 1000 nm. In certain embodiments, the SNP is KCC-1 (nanofibrous silica; having a size ranging from about 100 nm to about 1,000 nm). In certain embodiments, the KCC-1 has a size selected from the group consisting of about 100, 150, 200, 250, 300, 350, 400, 450, 500, 550, 600, 650, 700, 750, 800, 850, 900, 950, and about 1000 nm.

In certain embodiments, the TNP is mesoporous titania (having a size ranging from about 8 nm to about 1,000 nm). In certain embodiments, the mesoporous titania has a size selected from the group consisting of about 8, 50, 100, 150, 200, 250, 300, 350, 400, 450, 500, 550, 600, 650, 700, 750, 800, 850, 900, 950, and about 1000 nm. In certain embodiments, the TNP is colloidal titania (having a size ranging from about 8 nm to about 1,000 nm). In certain embodiments, the colloidal titania has a size selected from the group consisting of about 8, 50, 100, 150, 200, 250, 300, 350, 400, 450, 500, 550, 600, 650, 700, 750, 800, 850, 900, 950, and about 1000 nm.

In certain embodiments, the NP is non-porous. In certain embodiments, the NP comprises a plurality of pores. In certain embodiments, the NP is mesoporous.

In certain embodiments, the plurality of pores allow for loading of the cargo in the pores. In certain embodiments, the plurality of pores have dimensions suitable for receiving different cargoes having distinct chemical and physical (such as size and shapes) properties.

In certain embodiments, the cargo is a therapeutic cargo. In certain embodiments, the therapeutic cargo includes, for example, drugs, a metal species, and/or peptides having antibiotic properties. In certain embodiments, the therapeutic cargo includes, for example, a cleaning agent, a disinfecting agent, a preserving agent, healing agent, a bacteriostatic agent, an antifungal agent, and/or an antiviral agent.

In certain embodiments, the metal species comprises a metal nanoparticle. In certain embodiments, the metal comprises silver and/or copper. In certain embodiments, the copper is selected from the group consisting of Cu(0), Cu(I), and Cu(II). In certain embodiments, the Cu(0), Cu(I), or Cu(II) is derived from Cu(I) acetate (CuOAc), Cu(II) acetate (Cu(OAc)$_2$), or Cu(II) chloride (CuCl$_2$). In certain embodiments, the metal nanoparticle is within the pores of the NP. In certain embodiments, the cargo is a molecular marker and/or a biomarker. In certain embodiments, the molecular marker and/or biomarker detects for the presence of bacteria. In certain embodiments, the molecular marker and/or biomarker is selected from the group consisting of O$_2$, β-catenin and c-myc, and matrix metalloproteinases.

In certain embodiments, the bacteria includes, for example, *Staphylococcus aureus*/MRSA, *Streptococcus pyogenes, Escherichia coli, Enterococci* and/or *Pseudomonas aeruginosa*.

In order for the NPs to accommodate the therapeutic agents of distinct sizes and shapes, they have to be prepared under conditions that allow for tailoring the pore size/surface topography of the NPs. Therefore, in certain embodiments the dimensions of the pore are tailored by using a sol-gel method in the presence of surfactant templates.

In certain embodiments, the surfactant is a cationic surfactant. Non-limiting examples of cationic surfactants include cetyltrimethylammonium bromide (CTAB), cetyltrimethylammonium chloride (CTAC), cetylpyridinium chloride (CPC), cetylpyridinium bromide (CPB), 1-tetradecyl-3-methylimidazolium bromide (C$_{14}$MIMBr), 1-hexadecyl-3-methylimidazolium bromide (C$_{16}$MIMBr), 1-octadecyl-3- methylimidazolium bromide (C$_{18}$MIMBr), and 1-tetradecyloxymethyl-3-methylimidazolium chloride (C$_{14}$OCMIMCl), In certain embodiments, the surfactant is a non-ionic surfactant. Non-limiting examples of non-ionic surfactants include Pluronic P123, Pluronic F123, F127, Brij-76 surfactant, Triton X-100 Surfactant, and Tween 20, 40, 60 and 80 surfactants.

In certain embodiments, the surfactant is an anionic surfactant. Non-limiting examples of anionic surfactants include sodium dodecyl benzene sulfonate (SDBS), and sodium dodecyl sulphate (SDS).

In certain embodiments, the surface topography of the NP is further modified to improve its anti-adhesion properties against biofilms formed by microorganisms. Biofilm formation reduces accessibility of wounds to the therapeutic agents and hence, impeding biofilm formation can enhance the efficiency of treatment of wounds resulting in improved rate of wound healing.

In certain embodiments, the surface of NP is functionalized with at least one pH-responsive polymer and/or copolymer. Chronic wounds typically have a relatively alkaline pH environment of 7.15 to 8.90. Depending on the pH of the skin, the NPs functionalized with the pH-responsive polymer that can swell to release the cargoes and de-swell to constrain the release of the cargoes.

In certain embodiments, the at least one polymer/copolymer used for functionalizing the NPs of the disclosure is dendrimeric and has a relatively low molecular weight. Examples of polymer/copolymer include but are not limited to poly(N-isopropylacrylamide), poly(acrylic acid), poly (lactide-co-glycolide) (PLGA), polyethylene glycol, polyoxazoline, PAMAM dendrimers (Generation 2, 3, 4). In certain embodiments, the molecular weight of the at least one polymer/copolymer is less than 1 KDa. In one embodiment, for example, the polymer is dendrimeric polyethyleneimine polymer.

In certain embodiments, the at least one polymer/copolymer further comprises at least one cargo. In certain embodiments, the at least one cargo is as described elsewhere herein.

In certain embodiments, the swelling of the polymer and/or copolymer allow for release of the at least one cargo from the nanoparticle.

In certain embodiments, the swelling of the polymer and/or copolymer allow for release of the at least one cargo from the polymer/copolymer.

In certain embodiments, the nanoparticle and the at least one polymer and/or copolymer comprise independently selected cargoes.

In certain embodiments, the disclosure comprises a composition useful for treating wounds. The composition includes chitosan, sodium alginate, gelatin, grapeseed oil and aloe vera gel. In certain embodiments, the composition is capable of forming a film over the wound.

In certain embodiments, the composition comprises about 0.10 to about 0.25% of chitosan. In certain embodiments, the composition comprises 0.10%, 0.11%, 0.12%, 0.13%, 0.14%, 0.15%, 0.16%, 0.17%, 0.18%, 0.19%, 0.20%, 0.21%, 0.22%, 0.23%, 0.24% or 0.25% of chitosan. Chitosan is hydrophobic, known to promote tissue growth, and has bactericidal properties. Advantageously, in certain embodiments, chitosan enhances the composition's ability to heal wounds. In certain embodiments, chitosan adds mechanical stability to the film formed over the wound, since chitosan is rigid in nature.

In certain embodiments, the composition comprises about 0.10% to about 1% of sodium alginate. In certain embodiments, the composition comprises 0.10%, 0.15%, 0.20%, 0.25%, 0.30%, 0.35%, 0.40%, 0.45%, 0.50%, 0.55%, 0.60%, 0.65%, 0.75%, 0.85%, 1.0%, 1.25%, 1.5%, 1.75, or 2% of sodium alginate. Sodium alginate is a hydrophilic polymer, which is used to prevent maceration of the wound due to prolonged exposure to moisture from the wound exudate.

In certain embodiments, the composition comprises about 0.1% to about 0.5% of gelatin. In certain embodiments, the composition comprises 0.1%, 0.2%, 0.3%, 0.4%, or 0.5% of gelatin. Advantageously, in certain embodiments, gelatin promotes the proliferation of epithelial cells in skin, thereby promoting the wound healing.

In certain embodiments, the composition comprises about 0.01% to about 1% of grapeseed oil. In certain embodiments, the composition comprises 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, or 1.00%. Advantageously, in certain embodiments, the grapeseed oil promotes the inhibition of bacterial growth and accelerates the wound healing process especially in the inflammation phase. The acidic pH of the oil contributes to the ideal environment for fibroblastic activity, cell migration, cell proliferation, and reorganization of collagen, which aids the wound healing process.

In certain embodiments, the composition further comprises poly-vinyl alcohol (PVA). PVA is biologically inactive and has high chemical and mechanical resistance.

In other embodiments, the composition further comprises NPs of the disclosure. In yet other embodiments, the NPs of the disclosure promote healing of wounds.

In certain embodiments, the composition of the disclosure is stored inside a pressurized container as an emulsion mixture of a monomer and other components of the disclosure, wherein the emulsion is stabilized by a surfactant. In certain embodiments, the composition of the disclosure polymerizes on exposure to the air. In certain embodiments, the composition of the disclosure is delivered in the form of a foam and forms a polymeric matrix film on the skin area where it is applied to.

In certain embodiments, the polymeric matrix film is mechanically tensile and maintains its structure during movement and expansion of skin surrounding the wound.

In certain embodiments, the film remains adhered to the wound for at least about 7 days after application. In certain embodiments, the film can easily be removed if and when desired.

In certain embodiments, the composition is formulated for topical administration.

In certain embodiments, the composition is formulated for use as a cleaning agent, a disinfecting agent, a preserving agent, healing agent, a bacteriostatic agent, an antifungal agent, and/or an antiviral agent.

In certain embodiments, the composition is useful for healing of variety of wounds including but not limited to burns and chronic wounds in a subject. In certain embodiments, the composition of the disclosure can be employed in treatment of certain autoimmune diseases. In certain embodiments, the autoimmune disease includes psoriasis and eczema Additionally, in certain embodiment, the composition of the disclosure can be incorporated in cosmetics products.

In certain embodiments, the subject is a mammal. In certain embodiments, the mammal is a human.

As would be understood by one of skill, an emulsion comprises a mixture of two or more immiscible liquids (i.e., contains multiple phases). Emulsions are thus distinct from solutions, which contain one or essentially only one phase. In an emulsion, one of the liquids (the dispersed phase) is dispersed in the other (the continuous phase). In one type of emulsion, a continuous liquid phase surrounds droplets of water (for example, a water-in-oil emulsion). In another type of emulsion, oil is dispersed within a continuous water phase (for example, an oil-in-water emulsion). Similarly, emulsification is the process by which emulsions are prepared.

The emulsion of the disclosure may further comprise an emulsifier. Emulsions of the disclosure may also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size.

In one embodiment, the emulsion further comprises an emulsifier or emulgent. An emulsifier may also be a surfactant. In one embodiment, the emulsifier is a grapeseed oil. Other non-limiting examples of emulsifiers include polyglycerol polyricinoleate, sorbitan tri-stearate, polyglycerol stearate, sorbitan mono-stearate, sorbitan mono-palmitate, sorbitan mono-laurate, POE 20 sorbitan mono-laureate, POE 20 sorbitan mono-oleate, and POE 20 mono-stearate. Various concentrations of an emulsifier may be used with the present disclosure. For example, the compositions of the present disclosure may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

Methods

In one aspect, the disclosure provides a method of promoting healing of wound in a subject in need thereof. In certain embodiments, the method comprises dressing the wound with the composition of the disclosure. This can be achieved, for example, by administering to the subject an effective amount of the composition of the disclosure. In certain embodiments, the composition of the disclosure is as described elsewhere herein.

In certain embodiments, the composition of the disclosure is administered to the subject topically to promote healing of chronic wounds and burn wounds. In another embodiment, the wound is in the skin of the subject.

In certain embodiments, the composition is delivered from a pressurized container, wherein the composition is stored in the container as an emulsion mixture of monomers and active ingredients stabilized by surfactants.

The delivery of the composition may be continuous, periodic, a one-time event, or the composition may be both periodically administered and continuously administered to the subject on separate occasions.

Kits

In one aspect, the disclosure further provides a kit comprising at least one pharmaceutical composition of the disclosure, at least one applicator, and instructional material for use thereof. The instructional material included in the kit comprises instructions for carrying out the method of the disclosure.

In certain embodiments, disclosure provides a kit comprising a composition of the disclosure stored in a pressurized container, such that the composition of the disclosure can be directly dispensed from the container to a desired area in the form of a foam.

Dosing

The amount of the composition of the disclosure to be administered, for example, topically, depends on the particular indication desired. For example, the dose depends on the type of wound to be treated. The dose may be different, for instance, if the delivery of the composition is intended to reduce chronic wound as opposed to burn.

The particular dosage may also be dependent on the dosing regimen chosen. For example, the composition may be delivered continuously or periodically. Conversely, the composition may be administered as a single administration as a one-time event.

The concentration and ratio of NP in the composition may vary. For example, a composition may contain a NP in a w/w ratio of from about 5 to about 95%, from about 10 to about 90%, from about 20 to about 90%, from 50 to about 90%, from about 60 to about 80%, from about 60 to about 75%, from about 20 to about 80%, from about 25 to about 75%, from about 30 to about 70%, from about 40 to about 60%, from about 1 to about 15%, from about 1 to about 10%, from about 1 to about 5%, or any range derivable therein.

Those skilled in the art recognize, or are to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

It is contemplated that any embodiment discussed in this specification can be implemented with respect to any method or composition of the disclosure, and vice versa. Furthermore, compositions of the disclosure can be used to achieve methods of the disclosure.

The following examples further illustrate aspects of the present disclosure. However, they are in no way a limitation of the teachings or disclosure of the present disclosure as set forth herein.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples, therefore, specifically point out the preferred embodiments of the present disclosure, and are not to be construed as limiting in any way the remainder of the disclosure.

The experimental procedures involved to produce the materials described above are illustrated with the figures below and described with examples below.

Example 1: Synthesis of Inorganic Nanomaterials

Inorganic nanostructured materials with silicon dioxide (i.e. silica or $SiO_2$) and titanium dioxide (i.e. titania or $TiO_2$) compositions are used as the base-materials for functionalized compositions. Both $SiO_2$ and $TiO_2$ are biocompatible. Variants of the silica and/or titania structures are described herein:

a. Silica (Porous and Non-Porous)
  i. MCM-41, MCM-48 type mesoporous silica (with sizes of 8 nm-1,000 nm)
  ii. SBA-15 type mesoporous silica (with sizes of 8 nm-1,000 nm)
  iii. Large pore mesoporous silica
  iv. Colloidal silica (with sizes of 8 nm-1,000 nm)
  v. Surface etched colloidal silica (with sizes of 8 nm-1,000 nm)
  vi. KCC-1 (nanofibrous silica) (with sizes of 100 nm-1,000 nm)
b. Titania (Porous and Non-Porous)
  i. Mesoporous titania (with sizes of 8 nm-1,000 nm)
  ii. Colloidal titania (with sizes of 8 nm-1,000 nm)

Materials Modifications

The sizes and pore structures of the silica and titania nanomaterials mentioned herein are modified by varying the synthetic parameters such as types of surfactants, size of surfactants, use of various hard templates, use of soft and hard templates together, additives and micelle-swelling agents, aging times, temperatures, etching pore walls and surfaces, and post-synthetic modifications.

The surfaces (external and internal surfaces) of silica and titania nanoparticles are chemically modified via surface functionalization with pH-responsive moieties which release cargoes (active pharmaceutical ingredients, antimicrobial peptides, etc.) and molecular markers and biomarkers such as $O_2$, β-catenin and c-myc, matrix metalloproteinases for the detection of presence of common bacterial species (such as *Staphylococcus aureus*/MRSA, *Streptococcus pyogenes, Escherichia coli, Enterococci* and *Pseudomonas aeruginosa*, etc.) in wounds.

Example 2: Characterization of Inorganic Nanomaterials

Functionalized nanoparticles structures are characterized for pore size, shape and size distribution to understand the effect of surface and pore structures of the materials on their ability to load and unload payloads of bioactive agents against wound harming microbes and for wound healing purposes. Thermal stability studies such as TGA and DSC are carried out to determine the degradation of grafted components on the silica or titania materials. X-ray diffraction, gas adsorption-desorption, transmission electron microscopy, and scanning electron microscopy are used to determine the structures, morphology, porosity, pore volume, pore diameter and surface area of the silica or titania materials. Drug loading and release profiles are examined under conditions simulating conditions found in wounds.

Since maintaining a moisture balance is important for wound healing, gaseous and liquid permeability are also assessed.

Example 3: Synthesis of Nanoparticles (NPs)

Synthesis of Cu/SBA-15 systems

Mesoporous SBA-15 type silica nanoparticles were synthesized by following the method previously reported by Zhang, et al. (2015, Chem. Comm. 51(89):16135-16138). The surfactant in the nanomaterials was removed via calcination. The resulting calcined SBA-15 was then functionalized with N-(2-aminoethyl)-3-aminopropyltrimethoxysilane (DAMO). Typically, 200 mg of calcined SBA-15 was sonicated in 30 mL of toluene for 20 min before 35 μL of DAMO was added into it. The mixture was stirred for 24 h at room temperature. The solid product was separated via centrifugation and then washed with ethanol three times to remove the residual or non-grafted DAMO. The washing was carried out by centrifuging the mixture (for 15 min at 5000 rpm) and then decanting the supernatant. The solid product was dried at 50° C. in air for 24 h. It was then mixed with 20 mL of 0.1 M of Cu(II) acetate and stirred for 24 h at room temperature (alternatively, Cu(II) chloride, or any of a number of alternative Cu(II) salts may be used). The mixture was centrifuged, and the excess Cu(II) was decanted. To remove residual Cu(II) ions from the sample, it was sonicated in DI water and centrifuged for 15 min at 5000 rpm. This was done twice to ensure that only anchored Cu(II) ions were left in the SBA-15 material. A bluish colored material, which is Cu(II)-loaded SBA-15 particles and which is named Cu(II)/SBA-15, was finally obtained.

Figure 4A:
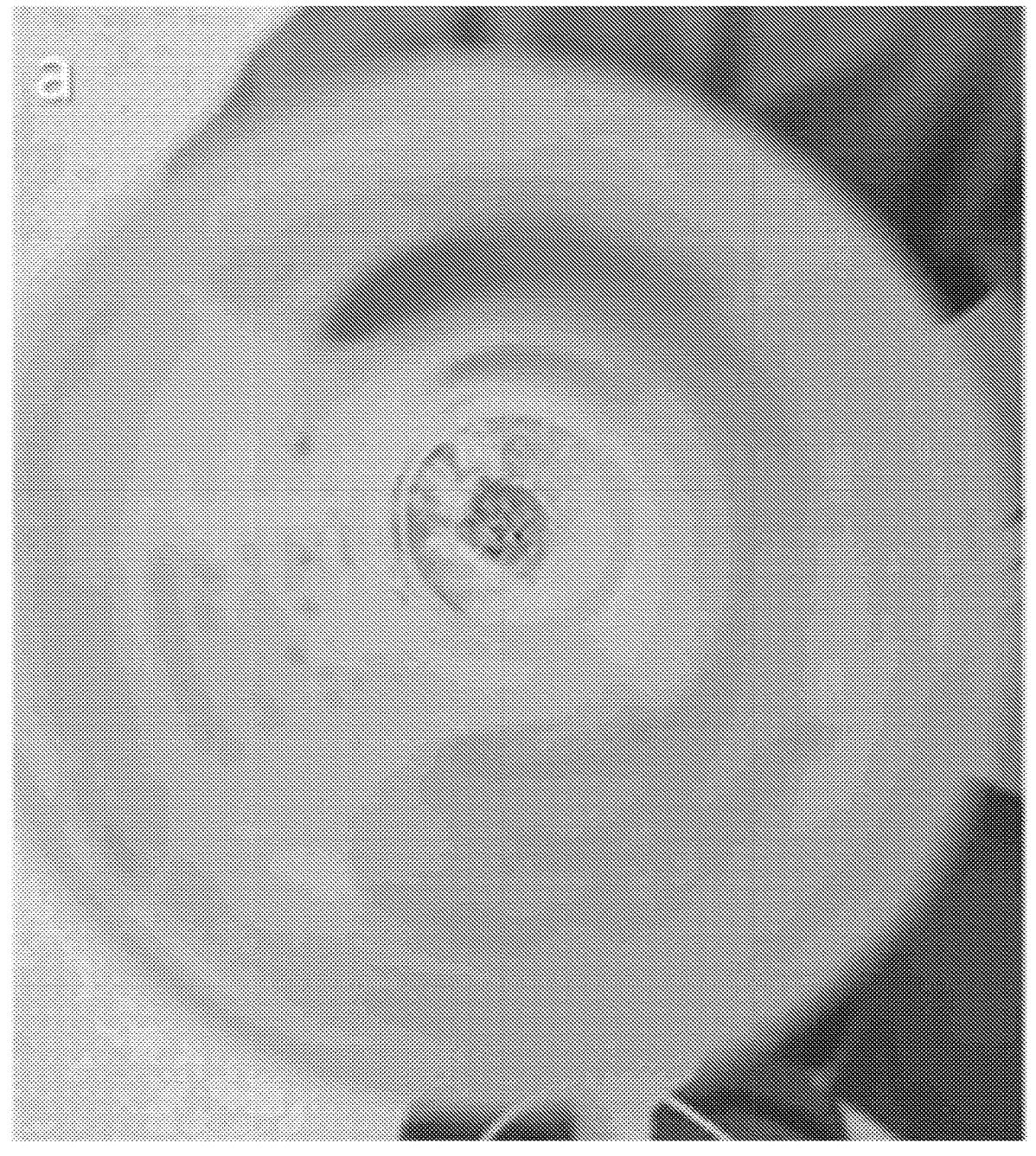
FIGS. 4A-4B comprise images of Cu(II)/SBA-15 and Cu/SBA-15.
Figure 4B:
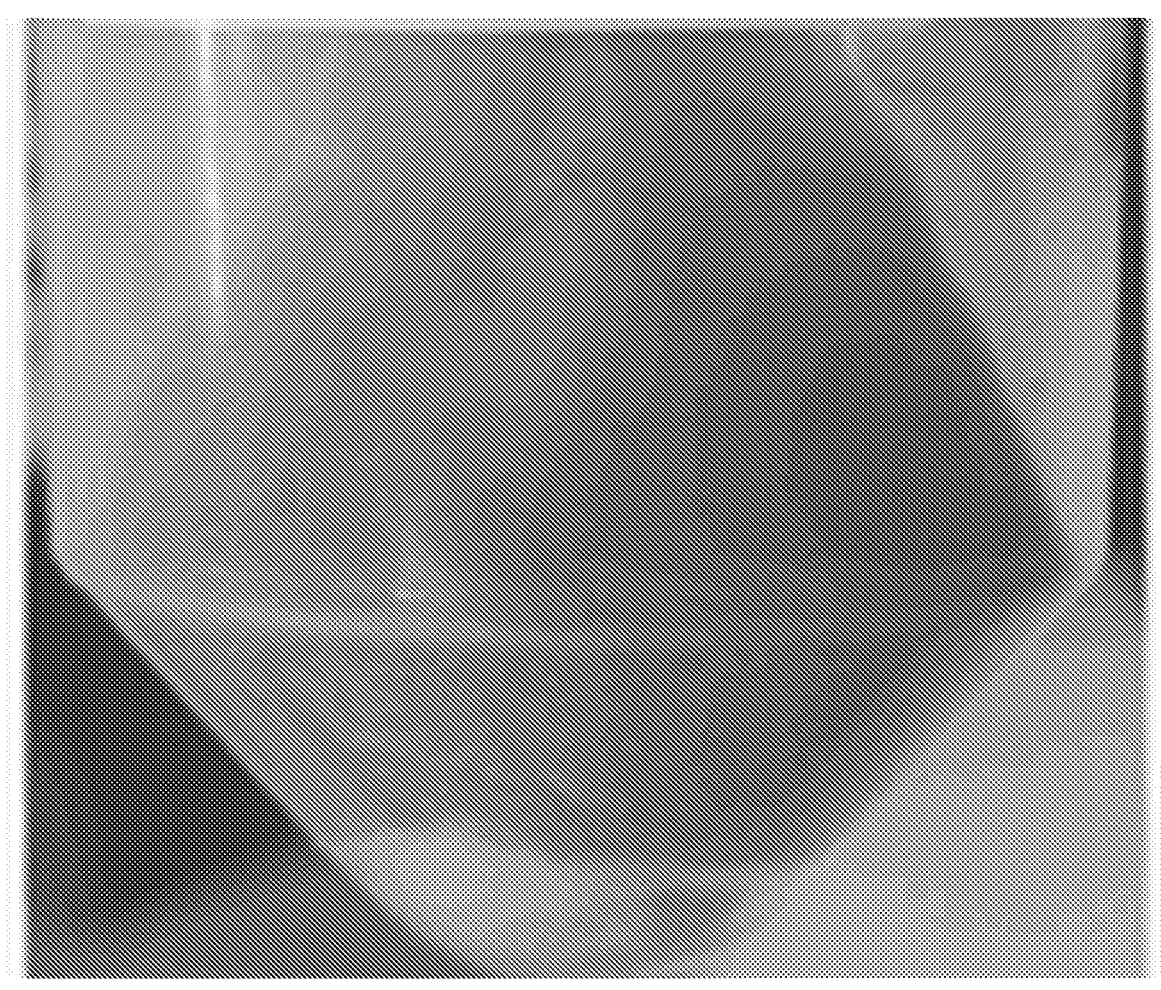

To reduce the Cu(II) ions loaded in Cu(II)/SBA-15, the sample was dispersed in an aqueous solution of 0.1 M L-ascorbic acid, and the mixture was stirred for 24 h at 90° C. The color of the sample changed slowly from blue ($Cu^{2+}$) to reddish-brown, indicating the reduction of Cu(II) into Cu(0) and the formation of $Cu^0$ nanomaterials within SBA-15 (FIGS. 4A-4B). The resulting reddish-brown-colored material was named Cu/SBA-15.

Synthesis of Methyl-Capped Cu/SBA-15 Nanomaterials

The as-synthesized SBA-15 material, which still contained Pluronic 123 templates, was treated with a solution of hexamethyldisilazane (HMDS)/toluene (5 mL/60 mL) under a $N_2$ atmosphere for 12 h. This allowed the external surface silanol groups of the as-synthesized SBA-15 to be capped with methyl (Me) groups. The Pluronic 123 templates were then removed from this sample via solvent extraction, by stirring 0.5 g of Me-capped mesostructured SBA-15 in 100 mL of a 1:1 mixture of diethyl ether and ethanol for 5 h. This yielded mesoporous SBA-15 Pluronic 123 templates in the channel pores and methyl groups on its external surface.

Example 4: Characterization of Nanoparticles

Figure 5:
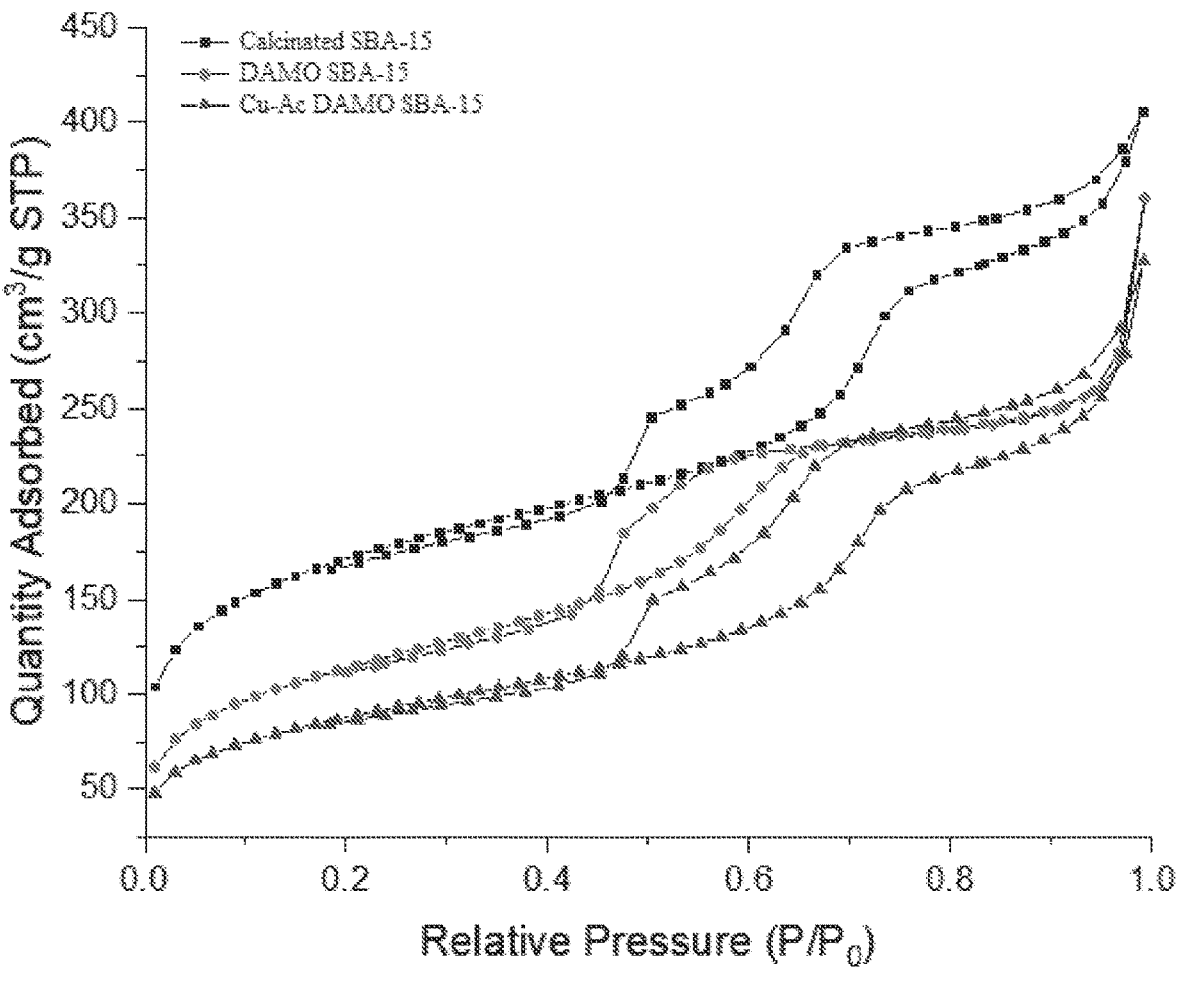
FIG. 5 illustrates gas adsorption isotherms for calcined SBA-15 (square), diamino-functionalized SBA-15 (or DAMO-SBA-15) (circle), and Cu/SBA-15 (triangle).

Gas adsorption analysis for calcined SBA-15, DAMO-functionalized SBA-15, and $Cu^0$-SBA-15 materials are shown in FIG. 5. Surface area and pore size for the materials are shown in Table 1. From the gas adsorption isotherms, all the materials appeared to be mesoporous, with some micropores being present. The surface areas of the materials decreased as organic functional groups (amine from DAMO) and copper were added into the channel pores of SBA-15. This also indirectly indicates the functionalization of the SBA-15 pore structures with organic groups and copper. Without wishing to be limited by any theory, the increase in pore size as copper is reduced in situ in the silica system may be attributed to internal strain in the pore as Cu nanoparticles (Cu NPs) NPs are formed. From surface area measurements, a 20% loading of Cu NPs was estimated.

TABLE 1

Surface area and average pore size for synthesized materials.
BET Surface Area and BJH Average Pore Sizes

| Samples | Surface Area ($m^2/g$) | Pore Size (nm) |
|---|---|---|
| Calcined SBA-15 | 568 | 5 |
| DAMO-modified SBA-15 | 402 | 5 |
| Cu(II)-DAMO-SBA-15 | 308 | 6 |

Figure 6A:
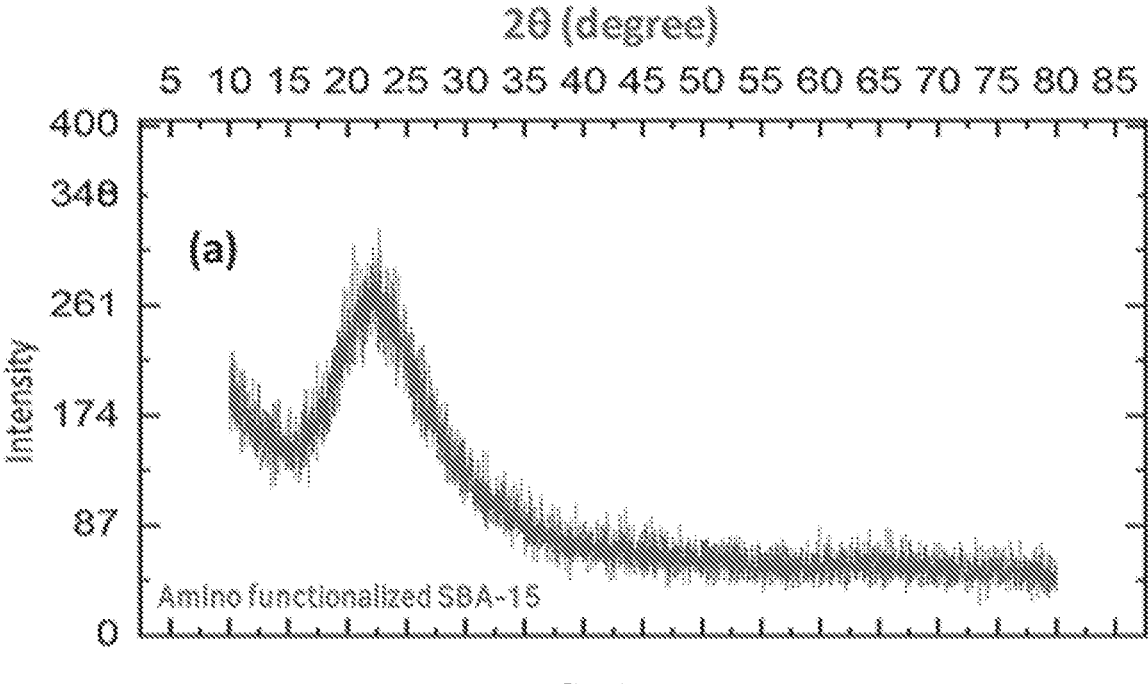
FIGS. 6A-6B illustrate wide-angle XRD patterns of DAMO-functionalized-SBA-15 (FIG. 6A), where no characteristic peaks associated with Cu is seen and Cu/SBA-15, and DAMO-functionalized-SBA-15 comprising Cu⁰, which shows sharp, distinct peaks corresponding to metallic Cu (FIG. 6B).
Figure 6B:
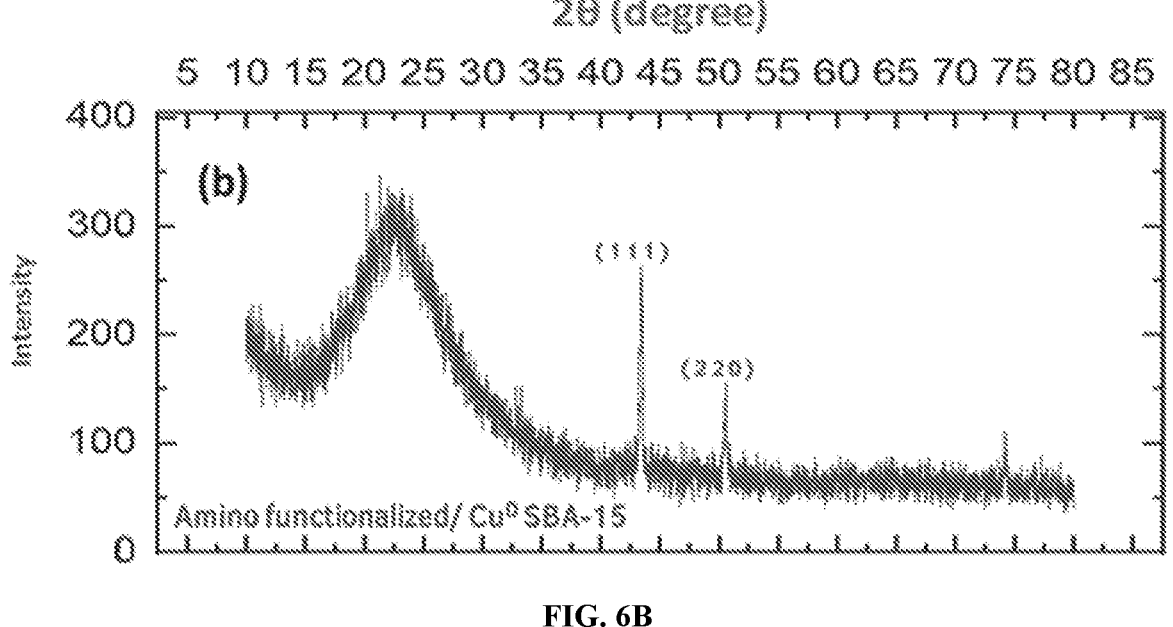

To confirm the presence and formation of metallic Cu in Cu-DAMO-SBA-15 after treatment of Cu-DAMO-SBA-15 with ascorbic acid, the material was characterized by X-ray diffraction (XRD) before and after the reduction. XRD patterns of the former (i.e. amino functionalized SBA-15) and the latter (i.e. amino functionalized $Cu^0$ SBA-15) are provided in FIGS. 6A-6B, respectively. There are two distinct peaks (2θ=45 and 50°) that correspond to metallic copper ($Cu^0$) nanoparticles (or Cu NPs) in Cu/SBA-15. Nanometer sized particles usually exhibit smaller, broader peaks than the ones presented herein. In certain embodiments, Cu NPs can grow outside the SBA-15 pore, allowing it to form larger particles on the SBA-15 surface. Using the Scherrer equation, the sizes of the Cu NPs was determined to be 34 nm, nearly six times larger than the reported SBA-15 pore size of 6 nm. This indicates that there were some larger Cu NPs grown outside the channel pores of the materials. In certain embodiments, hexamethyldisilazane (HMDS) can be used to protect the outer surfaces. In certain embodiments, such treatment leads primarily to growth of CuNPs in the channel pores of the materials.

Figure 7:
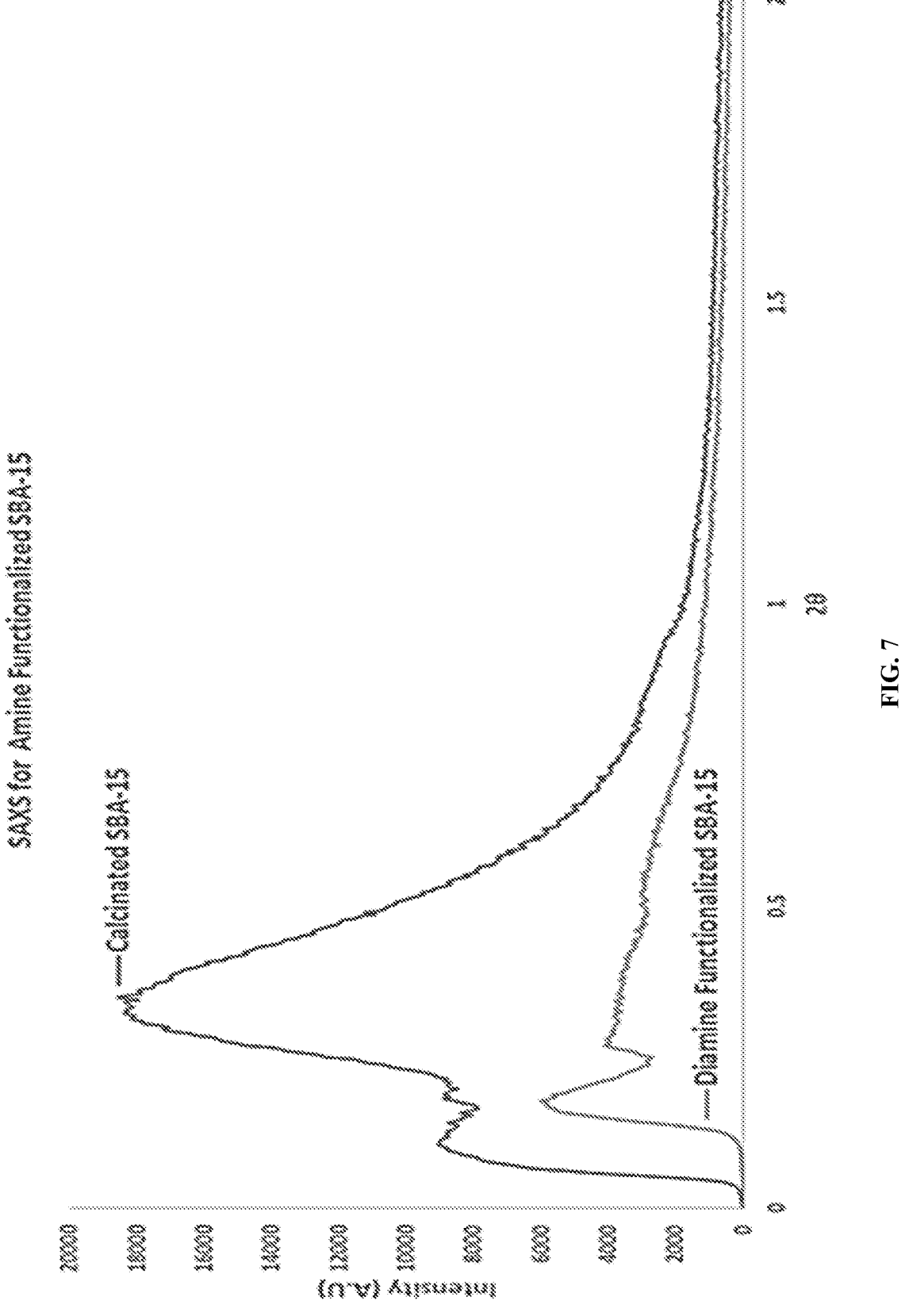
FIG. 7 illustrates small-angle X-ray scattering patterns of calcined SBA-15 and diamine functionalized-SBA-15 (DAMO-SBA-15).

From the small angle X-ray scattering experiments XRD patterns, it was observed that the SBA-15 maintains its ordered structure (2θ=22°), since no notable shifts in the diffractogram are present (FIG. 7).

In order to more adequately control the sizes of the Cu nanoparticle (Cu NP) in the SBA-15, the outer surfaces of the SBA-15 can be capped with methyl (Me) groups, thereby only growing them only in the channel pores of SBA-15, as the methyl groups on the outer surface prevent the growth of Cu nanoparticles. This functionalization also makes the previously hydrophilic surface hydrophobic and force the aqueous copper solution inside the particle pore. To achieve this, the external surfaces of the material were functionalized with methyl groups before removing the surfactant from the silica channel pores of via solvent extraction. This makes the silanol groups present only in inside pores of SBA-15 silica pore (Silva, et al., 2011, J. Phys. Chem. C, 115(46): 22810-22817). In certain embodiments, functionalization with amine (—$NH_2$) groups takes place only inside pores of SBA-15 silica pore. The amine groups within the silica pores can serve as anchors for copper ions that are later reduced using L-ascorbic acid at 0.1 M for 24 h at 90° C.

Figure 8:
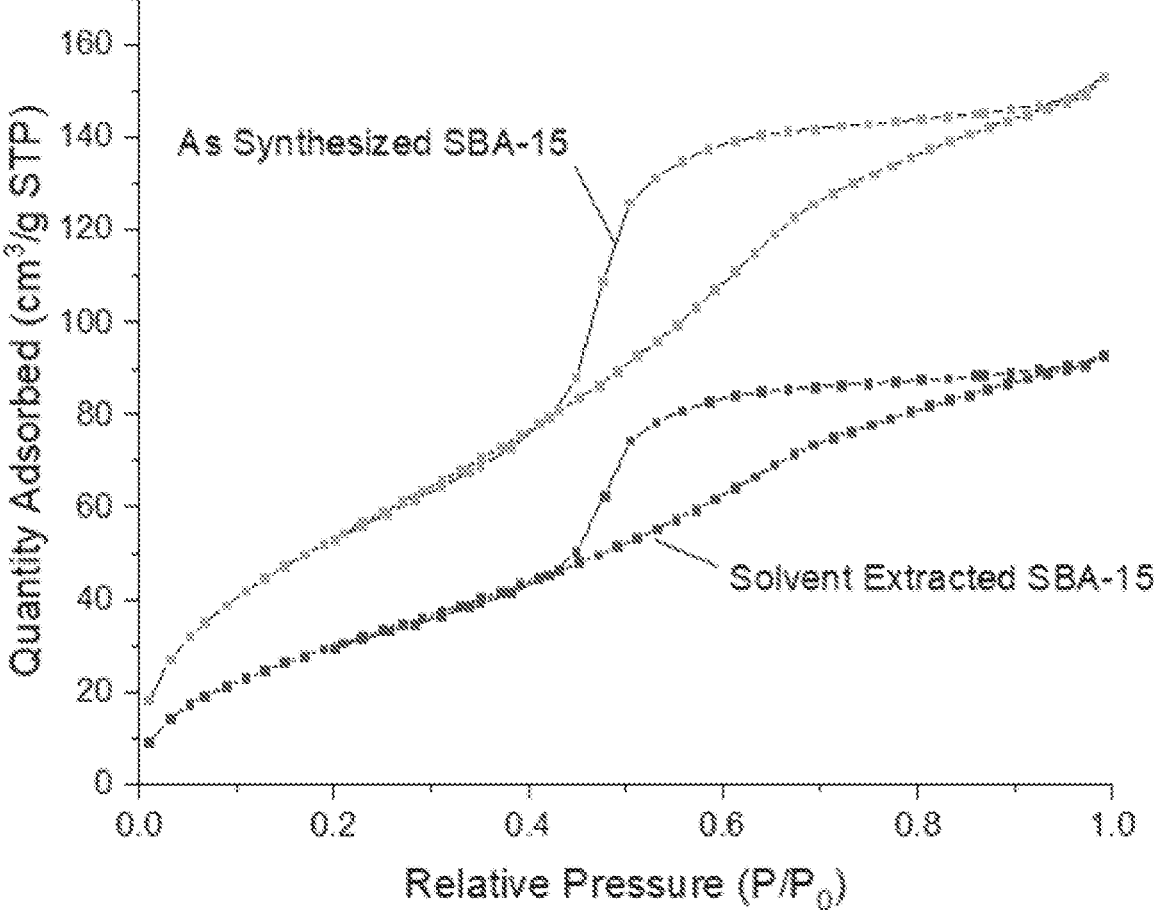
FIG. 8 illustrates gas adsorption analysis for as synthesized methyl capped SBA-15 and solvent extracted methyl capped SBA-15.

Preliminary results for gas adsorption for as synthesized methyl capped SBA-15 and solvent extracted methyl capped SBA-15 are shown below in FIG. 8. The materials appeared mesoporous with hardly any microporous structures present. Surface area for the materials are shown in Table 2. A 50% increase in surface area was shown for the solvent extracted materials, indicating that the pores were emptied of surfactant. No significant pore size reduction was observed.

TABLE 2

Surface area and average pore size for synthesized materials.
BET Surface Area and average pore size

| Samples | Surface Area $(m^2/g)$ | Average Pore Size |
|---|---|---|
| As Synthesized Methyl Capped SBA-15 | 122 | 4 nm |
| Solvent Extracted Methyl Capped SBA-15 | 213 | 4 nm |

In certain non-limiting embodiments, silica pore walls serve as a size restriction and limit Cu NP growth not to exceed the SBA-15 pore size.

Example 5: Biological Studies

Effect of SBA-15 NPs on Gram Positive Bacteria

Figure 9:
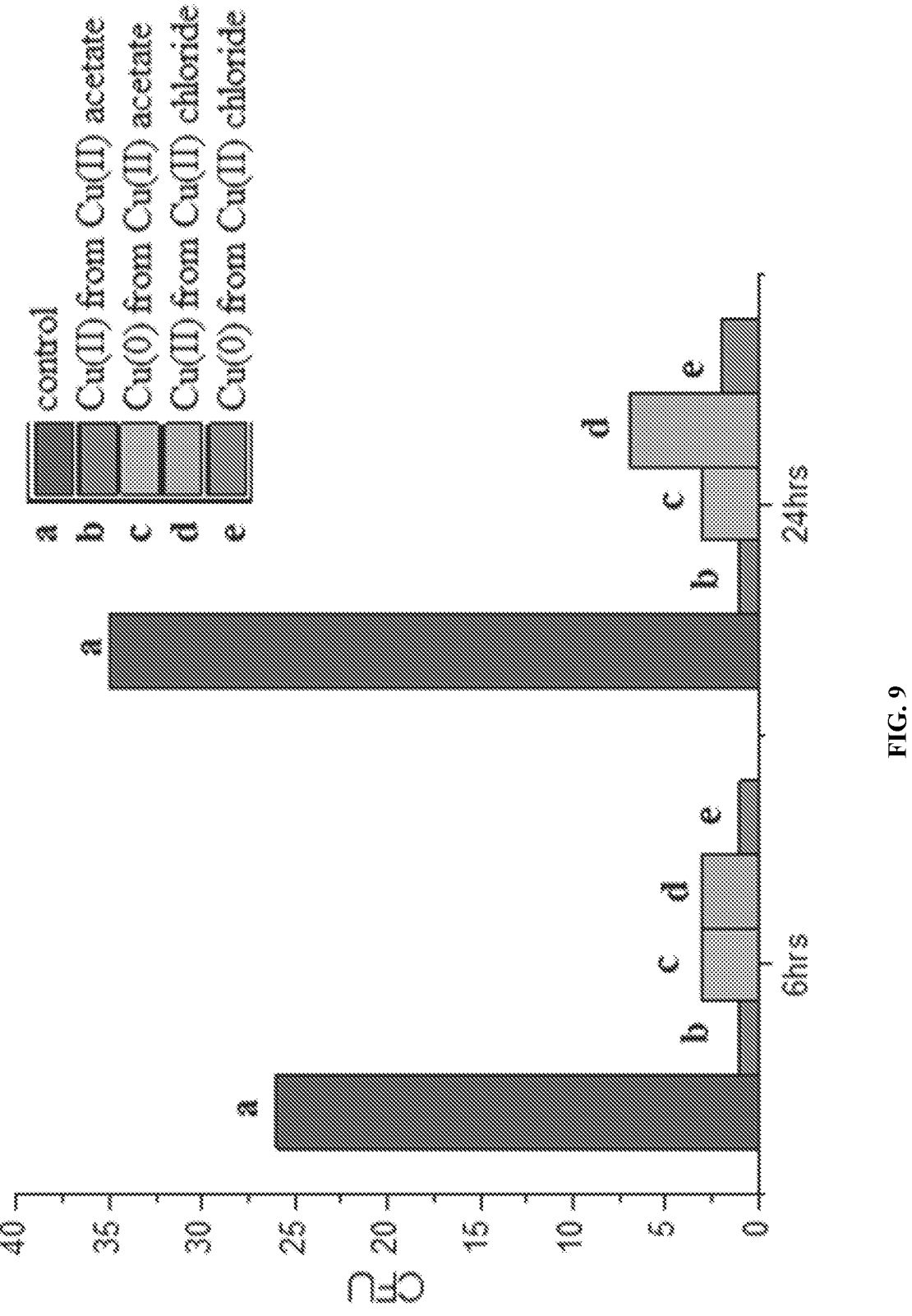
FIG. 9 shows preliminary bacterial colony counts (colony forming units or CFU) of *Staphylococcus aureus* from the last dilution after treatment with different copper-functionalized SBA-15 nanoparticles (4 mg/mL) for 6 h and 24 h. A control sample, which is not treated with any material, has been included for reference.
Figure 10A:
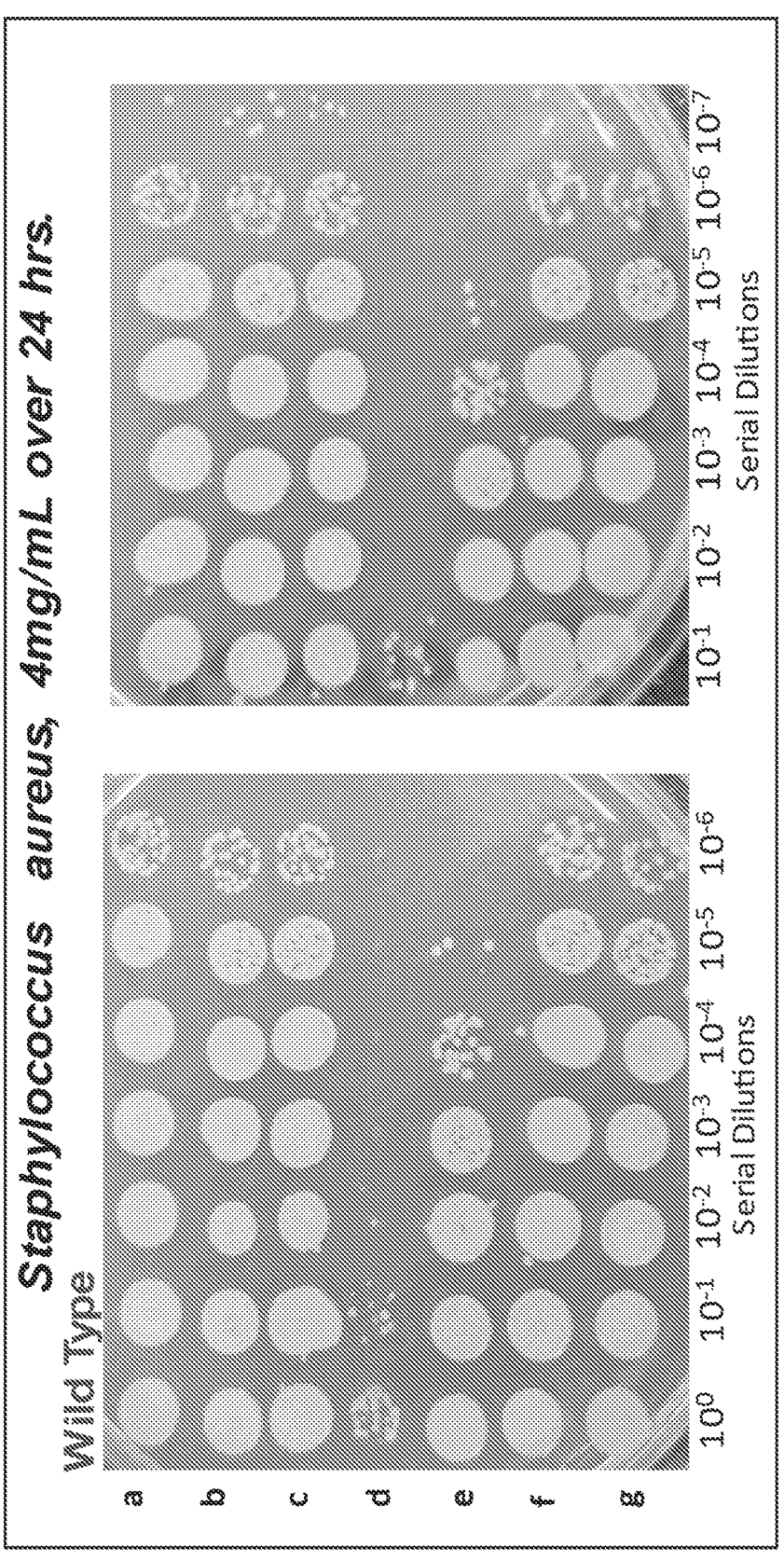
FIGS. 10A-10B show bactericidal growth tests for *Staphylococcus aureus* strains in tryptic soy broth (TSB) for wild-type bacteria (FIG. 10A) and copper-sensitive bacteria (FIG. 10B) after 24 h in the presence of the NPs of the present disclosure, wherein each row corresponds to a NP, and each column represents a different dilution of bacteria. The concentration for each NP is held constant at 4 mg/mL. Rows: (a) control; (b) SBA-15; (c) SBA-15-DAMO; (d) SBA-15-DAMO Cu(II) from Cu(II) acetate; (e) SBA-15-DAMO Cu(0) from Cu(II) acetate; (f) SBA-15-DAMO Cu(II) from Cu(II) chloride; and (g) SBA-15-DMAO Cu(0) from Cu(II) chloride. Columns: the left-most row represents an initial aliquot of bacteria in media which is serially diluted to $10^{-6}$ and $10^{-7}$, for FIG. 10A and FIG. 10B, respectively.
Figure 10B:
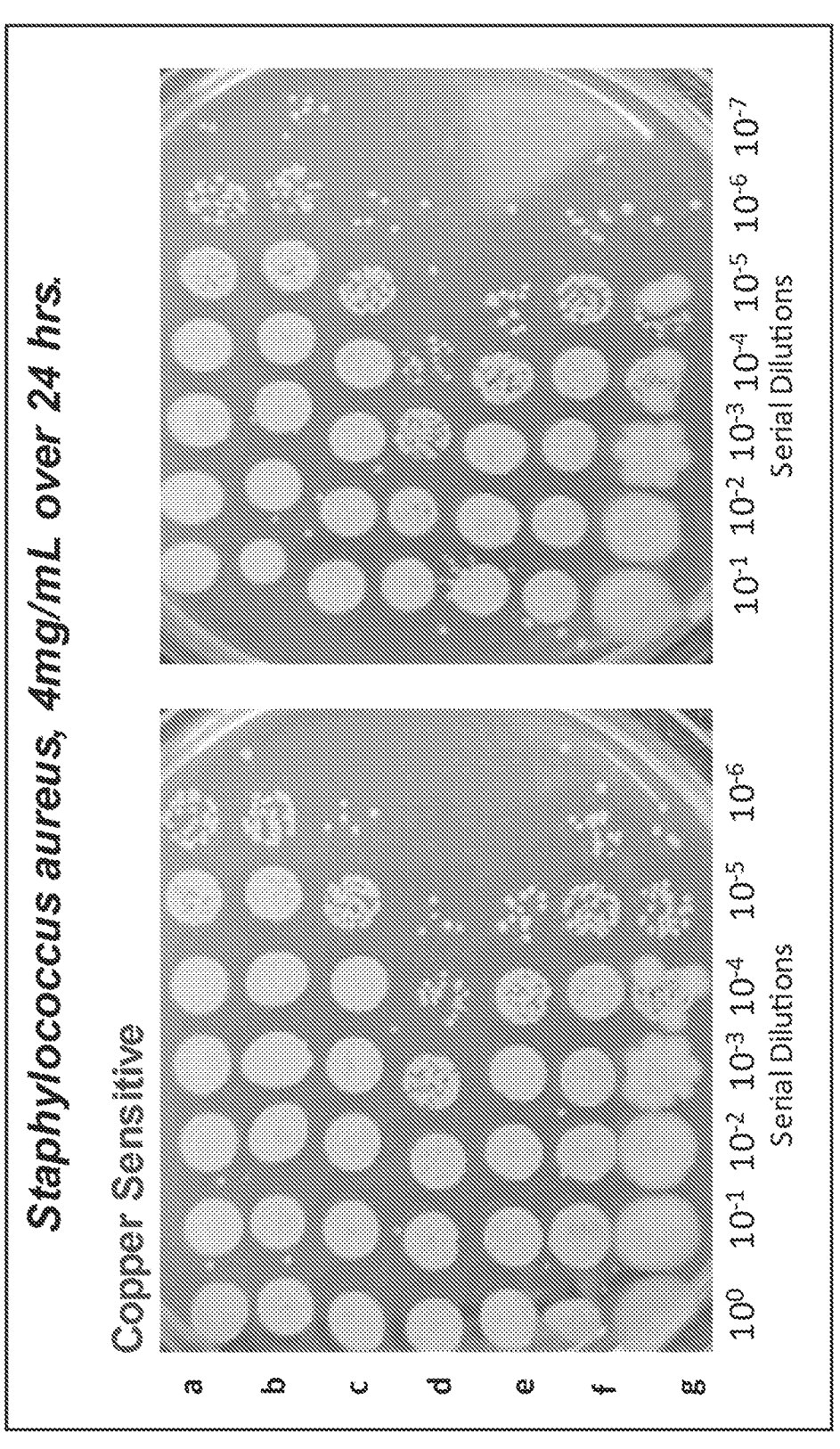

The effect of synthesized nanomaterials (i.e. NPs) on gram positive bacteria and the activity of the materials were investigated using wild-type *Staphylococcus aureus* as a model bacteria in tryptic soy broth (TSB) media (FIG. 9 and FIGS. 10A-10B).

While all copper functionalized nanomaterials presented unique antibacterial activity, Cu(II) acetate derived NPs demonstrated improved activity as compared to Cu(II) chloride derived NPs. Conversely, $Cu^0$ embedded NPs derived from Cu(II) chloride showed improved activity as compared to $Cu^0$ embedded NPs derived from Cu(II) acetate.

NPs derived from Cu(II) acetate demonstrated prolonged antibacterial activity as compared to NPs derived from Cu(II) chloride. However, all NPs exhibited effective antibacterial properties at 6 h or 24 h.

Effect of SBA-15 NPs on Gram Negative Bacteria

Figure 11:
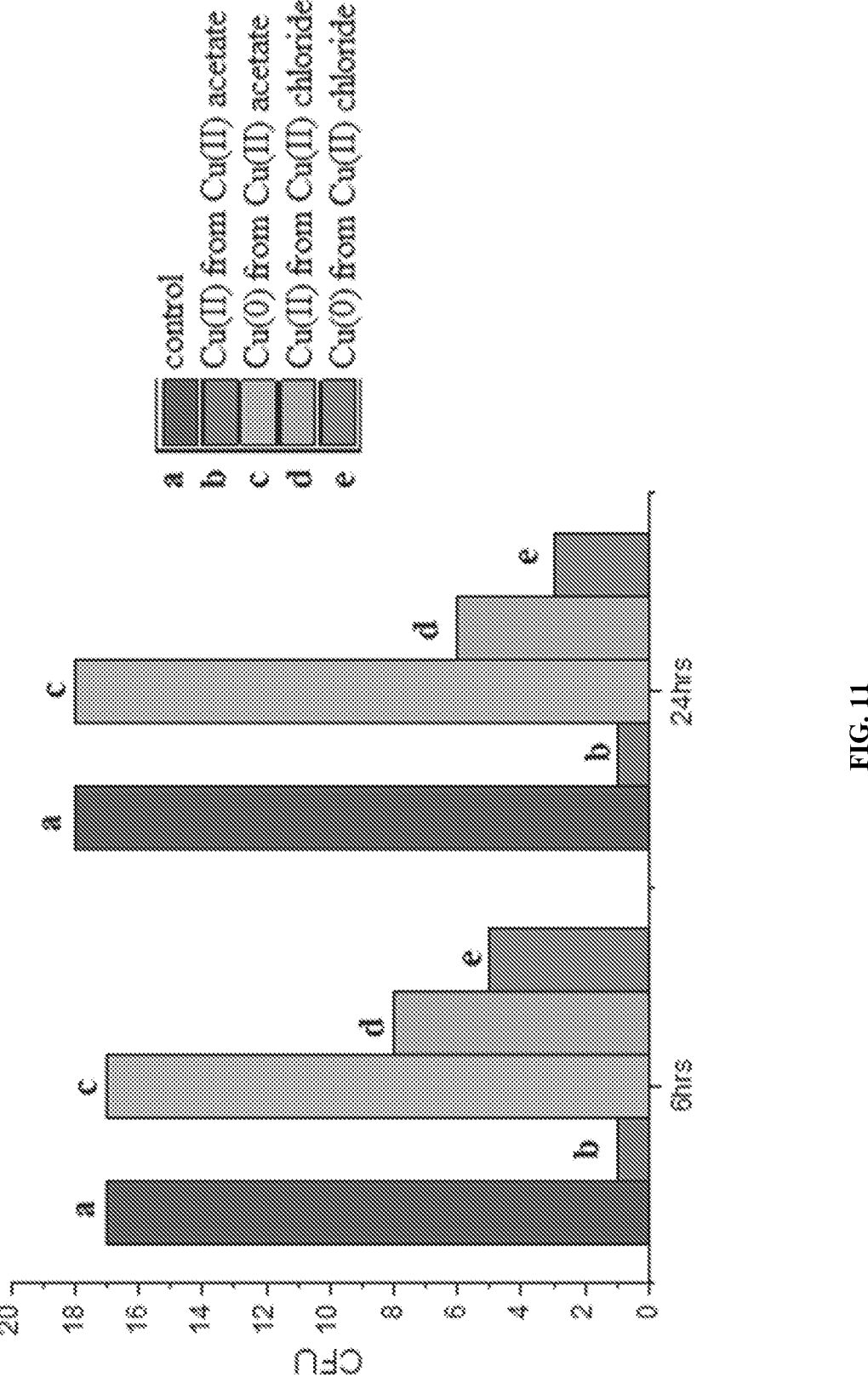
FIG. 11 shows preliminary bacterial colony counts (colony forming units or CFU) of *Escherichia coli* from the last dilution for copper-functionalized SBA-15 nanoparticles (4 mg/mL) at 6 h and 24 h.
Figure 12A:
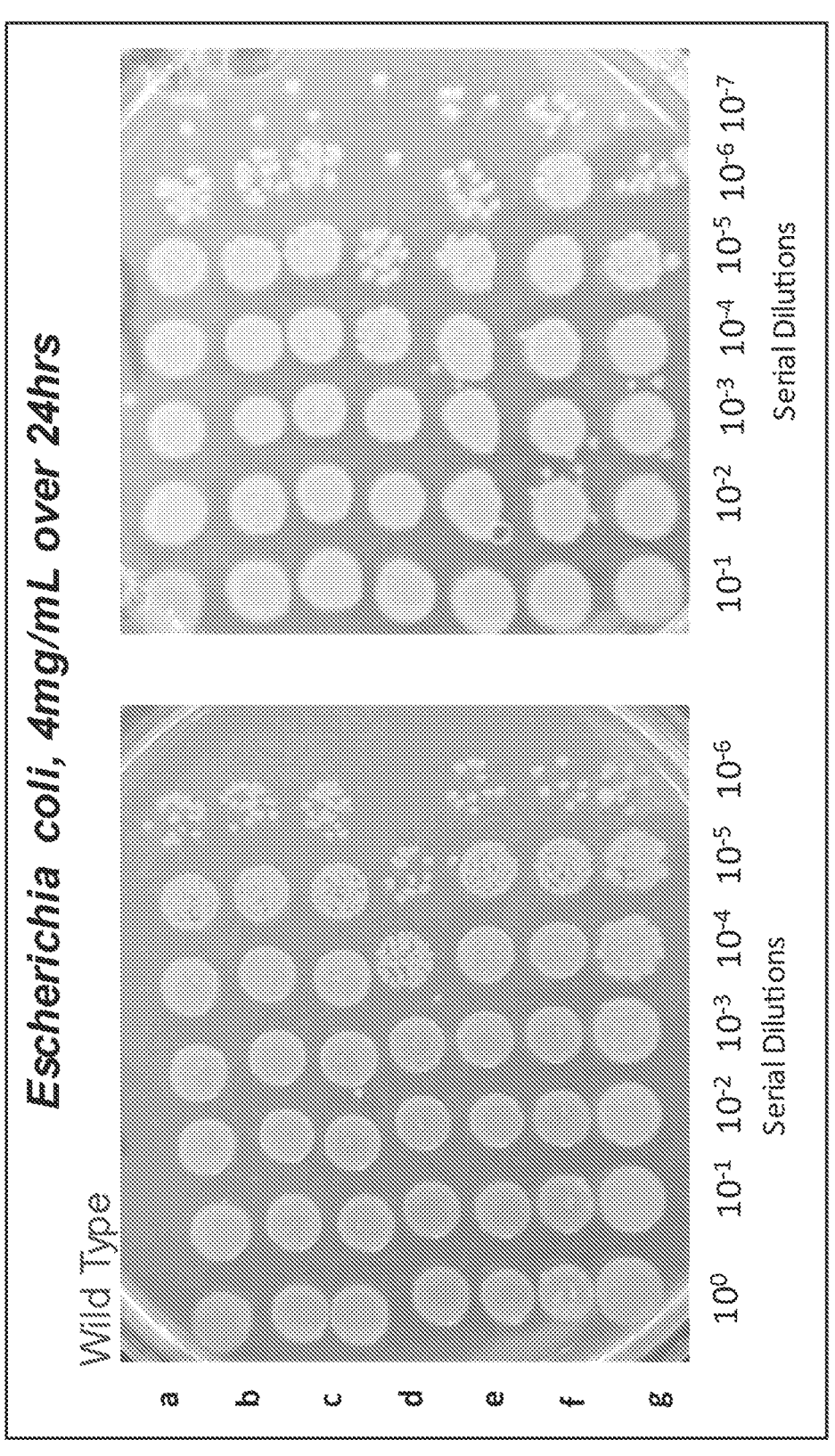
FIGS. 12A-12B show bactericidal growth tests for *Escherichia coli* strains in tryptic soy broth (TSB) for wild-type strains (FIG. 12A) and copper-sensitive strains (FIG. 12B) after 24 h, in the presence of the NPs of the present disclosure, wherein each row corresponds to a NP, and each column represents a different dilution of bacteria in media. The concentration for each NP is held constant at 4 mg/mL. Rows: (a) control; (b) SBA-15; (c) SBA-15-DAMO; (d) SBA-15-DAMO Cu(II) from Cu(II) acetate; (e) SBA-15-DAMO Cu(0) from Cu(II) acetate; (f) SBA-15-DAMO Cu(II) from Cu(II) chloride; and (g) SBA-15-DAMO Cu(0) from Cu(II) chloride. Columns: the left-most row represents an initial aliquot of bacteria in media which is serially diluted to $10^{-6}$ and $10^{-7}$, for FIG. 12A and FIG. 12B, respectively.
Figure 12B:
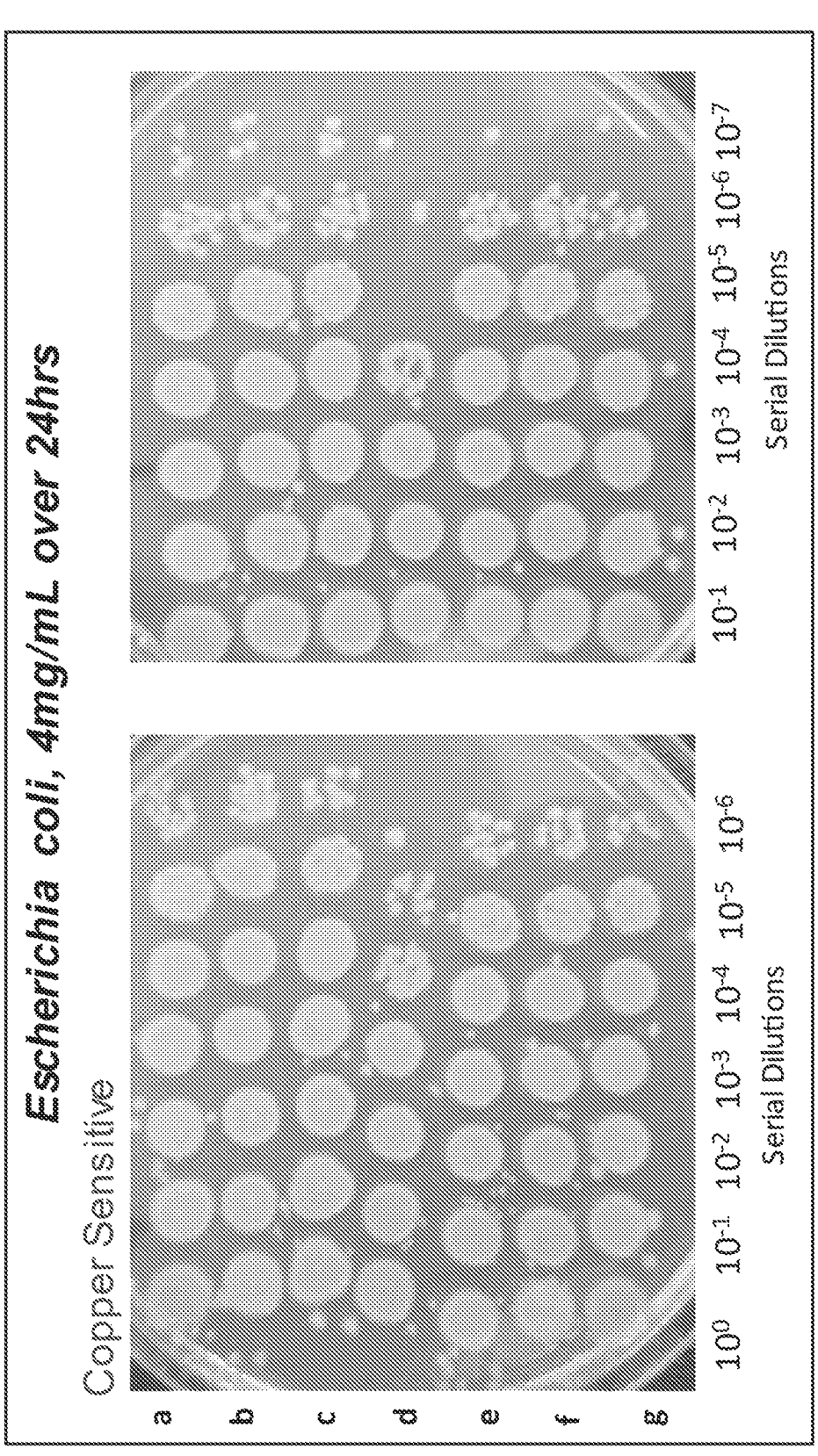

The effect of synthesized nanomaterials (i.e. NPs) on gram negative bacteria and the activity of the materials were investigated using wild-type *Escherichia coli* as a model bacteria in TSB media (FIG. 11 and FIGS. 12A-12B).

NPs derived from Cu(II) acetate (e.g. Cu(II) or Cu(0)) demonstrated marked differences in performance depending upon oxidation state, wherein the Cu(II) NP demonstrated improved bactericidal activity over the Cu(0) NP. Conversely, The difference in bactericidal activity for NPs derived from Cu(II) chloride was less significantly correlated with oxidation state.

Generally, the observed trend in bactericidal activity is Cu(II) from Cu(II) acetate>Cu(0) from Cu(II) chloride>Cu(II) from Cu(II) chloride>Cu(0) from Cu(II) acetate.

Effect of pH on Bactericidal Activity of SBA-15 NPs

Figure 13:
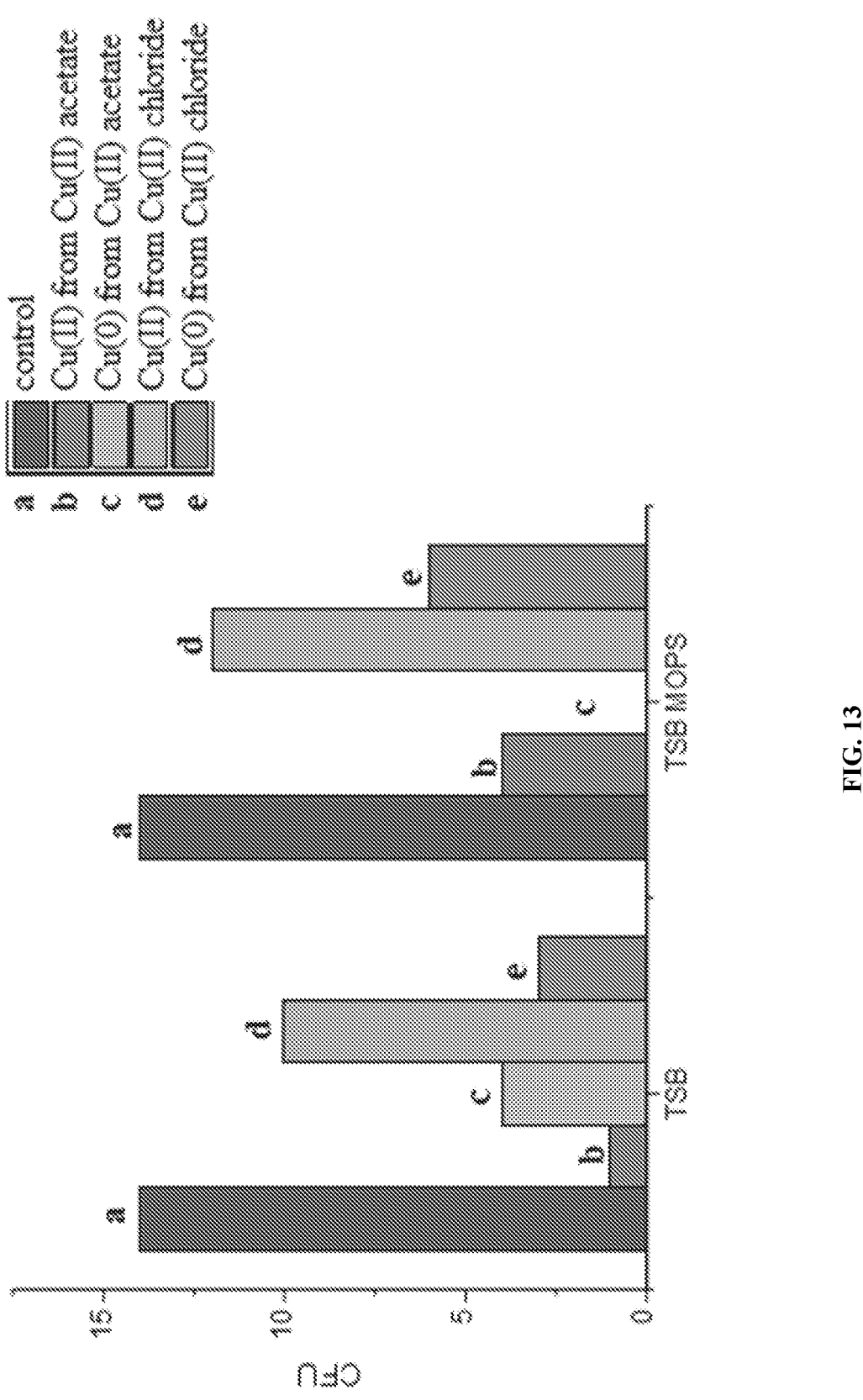
FIG. 13 shows preliminary bacterial colony counts (colony forming units or CFU) of *Staphylococcus aureus* from the last dilution treated with different copper-functionalized SBA-15 nanoparticles (4 mg/mL) in tryptic soy broth (TSB) with and without 3-(N-morpholino)propane sulfonic acid (MOPS) buffer at 24 h.
Figure 14:
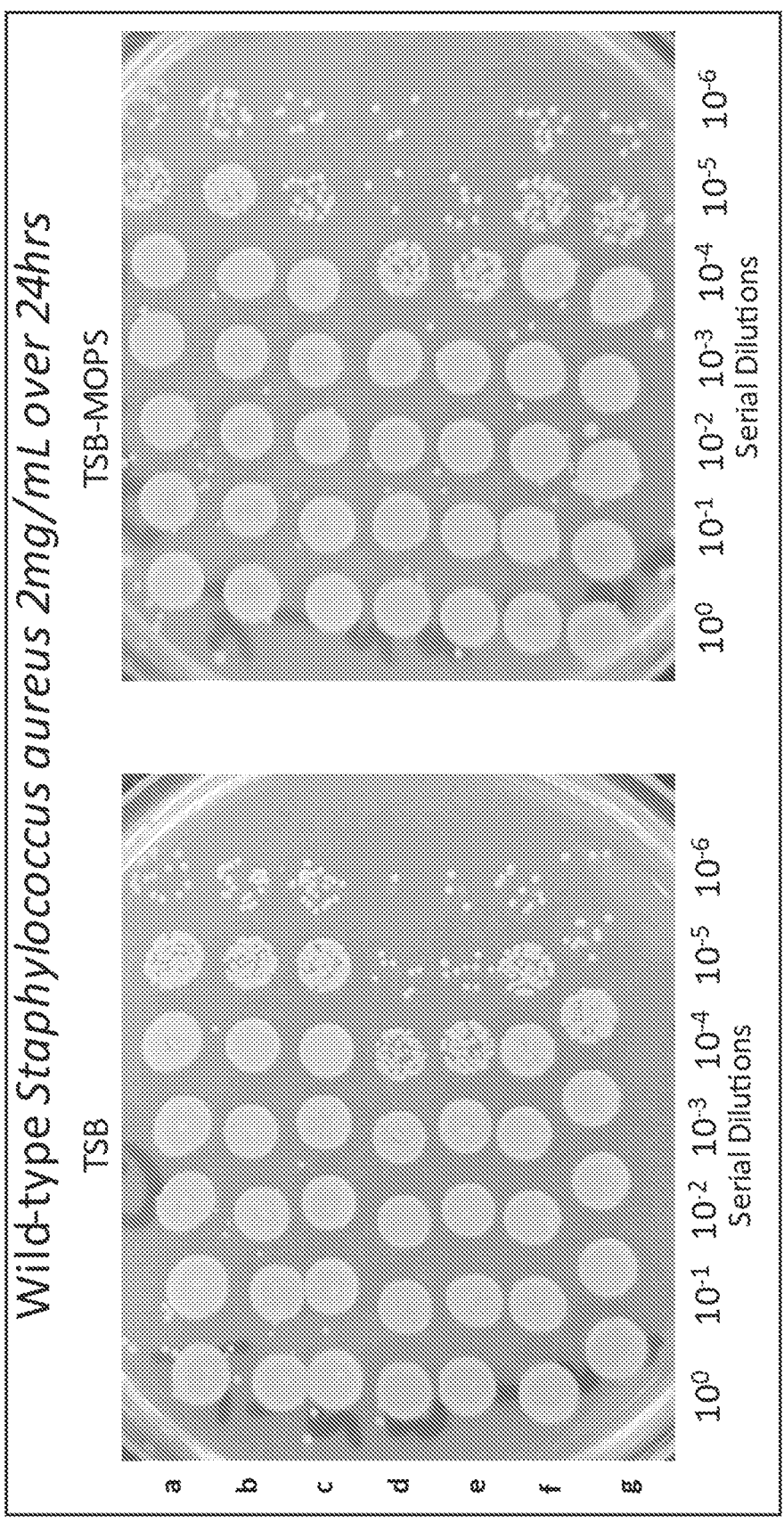
FIG. 14 shows bactericidal growth tests for wild-type *Staphylococcus aureus* strains in TSB or with TSB buffered with MOPS at 24 h, in the presence of the NPs of the present disclosure, wherein each row corresponds to a NP, and each column represents a serial dilution of bacteria in media. The concentration for each NP is held constant at 4 mg/mL, except for the control, wherein no NP is applied. Rows: (a) control; (b) SBA-15; (c) SBA-15-DAMO; (d) SBA-15-DAMO Cu(II) from Cu(II) acetate; (e) SBA-15-DAMO Cu(0) from Cu(II) acetate; (f) SBA-15-DAMO Cu(II) from Cu(II) chloride; and (g) SBA-15-DAMO Cu(0) from Cu(II) chloride. Columns: the left-most row represents an initial aliquot of bacteria in media which is serially diluted to $10^{-6}$ in the right-most row.

The effect of medium pH on the activity of NPs was investigated by using TSB (pH=7.3±0.2 at 25° C.) and TSB buffered with 3-(N-morpholino)-propane sulfonic acid (MOPS). Use of the buffered medium permitted investigation of the bactericidal effects within a range of pH values (pH 6.5-7.9) (FIG. 13 and FIG. 14).

While bactericidal activity was observed in both media, the NPs exhibited better overall performance in the unbuffered TSB medium, with the exception of NP bearing Cu(0)

derived from Cu(II) acetate. Without wishing to be bound by theory, a possible explanation for this discrepancy is that the bacteria may etch the metallic surface and cause leaching of the Cu(II) ions, which exhibit antimicrobial action.

Enumerated Embodiments

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

The following enumerated embodiments are provided, the number of which is not to be construed as designating levels of importance.

Embodiment 1 provides a nanoparticle (NP) functionalized with at least one pH-responsive polymer and/or copolymer, wherein at least one cargo is associated with the nanoparticle and/or the at least one pH-responsive polymer/copolymer, and wherein swelling of the at least one pH-responsive polymer and/or copolymer allows for release of the at least one cargo from the NP or the polymer and/or copolymer comprising the cargo, wherein the nanoparticle comprises a silica nanoparticle (SNP) or a titania nanoparticle (TNP), wherein the nanoparticle is:

(a) a porous nanoparticle comprising a plurality of pores, which allow for loading of the cargo in the plurality of pores, or (b) a non-porous nanoparticle; and wherein the cargo comprises at least one selected from the group consisting of a therapeutic cargo, a molecular marker, and/or a biomarker.

Embodiment 2 provides the NP of Embodiment 1, wherein the nanoparticle and the at least one polymer and/or copolymer comprise independently selected cargoes.

Embodiment 3 provides the NP of any of Embodiments 1-2, wherein the therapeutic cargo includes a small molecule drug, a metal species, or a therapeutic peptide, or any combination thereof.

Embodiment 4 provides the NP of Embodiments 3, wherein the therapeutic cargo comprises a metal nanoparticle.

Embodiment 5 provides the NP of Embodiment 4, wherein the metal nanoparticle comprises copper and/or silver.

Embodiment 6 provides the NP of Embodiment 5, wherein the copper is selected from the group consisting of Cu(0), Cu(I), and Cu(II).

Embodiment 7 provides the NP of Embodiment 6, wherein the Cu(0), Cu(I), or Cu(II) is derived from Cu(I) acetate (CuOAc), Cu(II) acetate $(Cu(OAc)_2)$, or Cu(II) chloride $(CuCl_2)$.

Embodiment 8 provides the NP of any of Embodiments 1-7, wherein the therapeutic cargo comprises at least one selected from the group consisting of cleaning agent, disinfecting agent, preserving agent, healing agent, bacteriostatic agent, antifungal agent, and antiviral agent.

Embodiment 9 provides the NP of any of Embodiments 1-8, wherein the molecular marker and/or biomarker detects the presence of bacteria.

Embodiment 10 provides the NP of Embodiment 9, wherein the bacteria comprises *Staphylococcus aureus/MRSA*, *Streptococcus pyogenes*, *Escherichia coli*, *Enterococci* and/or *Pseudomonas aeruginosa*.

Embodiment 11 provides the NP of any of Embodiments 1-10, wherein the molecular marker and/or biomarker is selected from the group consisting of $O_2$, β-catenin and c-myc, and matrix metalloproteinases.

Embodiment 12 provides the NP of any of Embodiments 1-11, wherein the dimensions of the plurality of pores are controlled by preparing the silica matrix by a sol-gel method in the presence of a surfactant template.

Embodiment 13 provides the NP of any of Embodiments 1-12, wherein the NP is modified at its outer surface to improve its anti-adhesion properties against biofilm-forming microorganisms.

Embodiment 14 provides the NP of any of Embodiments 1-13, wherein the molecular weight of the at least one pH-responsive polymer and/or copolymer is less than 1 kDa.

Embodiment 15 provides the NP of any of Embodiments 1-14, wherein the at least one pH-responsive polymer and/or copolymer is dendrimeric.

Embodiment 16 provides the NP of any of Embodiments 1-15, wherein the at least one pH-responsive polymer and/or copolymer is selected from the group consisting of polyethyleneimine (PEI), poly(N-isopropylacrylamide), poly (acrylic acid), poly(lactide-co-glycolide) (PLGA), polyethylene glycol, and polyoxazoline, PAMAM dendrimers.

Embodiment 17 provides the NP of any of Embodiments 1-16, wherein the NP is biocompatible.

Embodiment 18 provides the NP of any of Embodiments 1-17, wherein the porous NP is a mesoporous NP.

Embodiment 19 provides the NP of any of Embodiments 1-18, wherein the SNP is selected from the group consisting of MCM-41, MCM-48 type mesoporous silica (having size ranging from about 8 nm to about 1,000 nm), SBA-15 type mesoporous silica (having size ranging from about 8 nm to about 1,000 nm), large pore mesoporous silica, colloidal silica (having size ranging from about 8 nm to about 1,000 nm), surface etched colloidal silica (having size ranging from about 8 nm to about 1,000 nm), and KCC-1 (nanofibrous silica having size ranging from about 100 nm to about 1,000 nm).

Embodiment 20 provides the NP of any of Embodiments 1-19, wherein the TNP is selected from the group consisting of mesoporous titania (having size ranging from about 8 nm to about 1,000 nm), and colloidal titania (having size ranging from about 8 nm to about 1,000 nm).

Embodiment 21 provides a composition comprising about 0.10% to about 0.25% of chitosan, about 0.10% to about 2.0% of sodium alginate, about 0.1% to about 0.5% of gelatin, about 0.01% to about 1% of grapeseed oil, and Poly-vinyl-alcohol (PVA), and aloe vera gel, wherein the composition is formulated for application to a wound for promoting healing of the wound.

Embodiment 22 provides the composition of Embodiment 21, which further comprises the NP of any one of Embodiments 1-20.

Embodiment 23 provides the composition of any of Embodiments 21-22, wherein the wound comprises a burn wound or a chronic wound.

Embodiment 24 provides the composition of any of Embodiments 21-23, wherein upon application of the composition to the wound the composition forms a thin film on the wound.

Embodiment 25 provides the composition of Embodiment 24, wherein the film is mechanically tensile and maintains its structure during movement and expansion of skin surrounding the wound.

Embodiment 26 provides the composition of any of Embodiments 24-25, wherein the film can remain adhered to the wound for at least about 7 days after application.

Embodiment 27 provides the composition of any of Embodiments 21-26, wherein the composition is applied to the wound as a foam.

Embodiment 28 provides the composition of any of Embodiments 21-27, wherein the composition is formulated for topical administration.

Embodiment 29 provides the composition of any of Embodiments 21-28, wherein the composition is formulated for use as a cleaning agent, a disinfecting agent, a preserving agent, healing agent, a bacteriostatic agent, an antifungal agent, and/or an antiviral agent.

Embodiment 30 provides a method of healing a wound of a subject, the method comprising administering to the wound an effective amount of the composition of any of Embodiments 21-29.

Embodiment 31 provides the method of Embodiment 30, wherein the composition is administered from a pressurized container.

Embodiment 32 provides the method of any of Embodiments 30-31, wherein the composition is stored in the container as an emulsified mixture of monomers and active ingredients stabilized by surfactants.

Embodiment 33 provides the method of any of Embodiments 30-32, wherein the wound is a chronic wound or a burn wound.

Embodiment 34 provides the method of any of Embodiments 30-33, wherein the subject is a human.

Embodiment 35 provides a kit for healing wounds, the kit comprising the composition of any one of Embodiments 21-29 stored in a pressurized container and instructional material for use thereof.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A nanoparticle (NP) functionalized with at least one pH-responsive moiety, wherein at least one cargo is associated with the nanoparticle or the at least one pH-responsive moiety, and wherein swelling of the at least one pH-responsive moiety allows for release of the at least one cargo from the NP or the pH-responsive moiety comprising the cargo, wherein the nanoparticle comprises a silica nanoparticle (SNP) or a titania nanoparticle (TNP), wherein the nanoparticle is:
(a) a porous nanoparticle comprising a plurality of pores, which allow for loading of the cargo in the plurality of pores, or
(b) a non-porous nanoparticle;

wherein the pH-responsive moiety is selected from the group consisting of N-(2-aminoethyl)-3-aminopropyltrimethoxysilane (DAMO) and a polymer or copolymer selected from the group consisting of polyethyleneimine (PEI), poly(N-isopropylacrylamide), poly (acrylic acid), poly(lactide-co-glycolide) (PLGA), polyethylene glycol, and polyoxazoline, PAMAM dendrimers; and wherein the cargo comprises at least one selected from the group consisting of a therapeutic cargo, a molecular marker, and a biomarker.

2. The NP of claim 1, wherein the nanoparticle and the at least one polymer or copolymer comprise independently selected cargoes.

3. The NP of claim 1, wherein at least one of the following applies:

(a) the therapeutic cargo includes a small molecule drug, a metal species, or a therapeutic peptide, or any combination thereof;

(b) the therapeutic cargo comprises a metal nanoparticle.

4. The NP of claim 1, wherein the molecular marker or biomarker detects the presence of at least one bacterium.

5. The NP of claim 1, wherein the molecular marker or biomarker is selected from the group consisting of $O_2$, β-catenin and c-myc, and matrix metalloproteinases.

6. The NP of claim 1, wherein at least one of the following applies:

(a) the dimensions of the plurality of pores are controlled by preparing the silica matrix by a sol-gel method in the presence of a surfactant template;

(b) the NP is modified at its outer surface to improve its anti-adhesion properties against biofilm-forming microorganisms;

(c) the at least one pH-responsive moiety has a molecular weight less than 1 kDa;

(d) the at least one pH-responsive moiety is dendrimeric;

(e) the NP is biocompatible; and (f) the NP is mesoporous.

7. The NP of claim 1, wherein one of the following applies:

(a) the SNP is selected from the group consisting of MCM-41, MCM-48 type mesoporous silica (having size ranging from about 8 nm to about 1,000 nm), SBA-15 type mesoporous silica (having size ranging from about 8 nm to about 1,000 nm), large pore mesoporous silica, colloidal silica (having size ranging from about 8 nm to about 1,000 nm), surface etched colloidal silica (having size ranging from about 8 nm to about 1,000 nm), and KCC-1 (nanofibrous silica having size ranging from about 100 nm to about 1,000 nm); or (b) the TNP is selected from the group consisting of mesoporous titania (having size ranging from about 8 nm to about 1,000 nm), and colloidal titania (having size ranging from about 8 nm to about 1,000 nm).

8. A composition comprising about 0.10% to about 0.25% of chitosan, about 0.10% to about 2.0% of sodium alginate, about 0.1% to about 0.5% of gelatin, about 0.01% to about 1% of grapeseed oil, and Poly-vinyl-alcohol (PVA), and aloe vera gel, wherein the composition is formulated for application to a wound for promoting healing of the wound, wherein the composition further comprises a nanoparticle (NP) functionalized with at least one pH-responsive moiety, wherein at least one cargo is associated with the nanoparticle or the at least one pH-responsive moiety, and wherein swelling of the at least one pH-responsive moiety allows for release of the at least one cargo from the NP or the pH-responsive moiety comprising the cargo, wherein the nanoparticle comprises a silica nanoparticle (SNP) or a titania nanoparticle (TNP), wherein the nanoparticle is:

(a) a porous nanoparticle comprising a plurality of pores, which allow for loading of the cargo in the plurality of pores, or (b) a non-porous nanoparticle;

wherein the pH-responsive moiety is selected from the group consisting of N-(2-aminoethyl)-3-aminopropylt-rimethoxysilane (DAMO) and a polymer or copolymer; and wherein the cargo comprises at least one selected from the group consisting of a therapeutic cargo, a molecular marker, or a biomarker.

9. The composition of claim 8, wherein the wound comprises a burn wound or a chronic wound.

10. The composition of claim 8, wherein upon application of the composition to the wound the composition forms a thin film on the wound.

11. The composition of claim 10, wherein the film is mechanically tensile and maintains its structure during movement and expansion of skin surrounding the wound.

12. The composition of claim 10, wherein the film can remain adhered to the wound for at least about 7 days after application.

13. The composition of claim 8, wherein the composition is applied to the wound as a foam.

14. The composition of claim 8, wherein at least one of the following applies:

(a) the composition is formulated for topical administration; and (b) the composition is formulated for use as a preserving agent, a bacteriostatic agent, an antifungal agent, or an antiviral agent.

15. The NP of claim 3, wherein the therapeutic cargo comprises at least one selected from the group consisting of a preserving agent, a bacteriostatic agent, an antifungal agent, and an antiviral agent.

16. The NP of claim 3, wherein the metal nanoparticle comprises copper or silver.

17. The NP of claim 16, wherein the copper is selected from the group consisting of Cu(0), Cu(I), and Cu(II).

18. The NP of claim 17, wherein the Cu(0), Cu(I), or Cu(II) is derived from Cu(I) acetate (CuOAc), Cu(II) acetate $(Cu(OAc)_2)$, or Cu(II) chloride $(CuCl_2)$.

19. The NP of claim 4, wherein the at least one bacterium comprises *Staphylococcus aureus*/MRSA, *Streptococcus pyogenes, Escherichia coli, Enterococci* or *Pseudomonas aeruginosa*.

* * * * *